United States Patent
Kassiou et al.

(10) Patent No.: US 8,492,379 B2
(45) Date of Patent: Jul. 23, 2013

(54) TRANSLOCATOR PROTEIN LIGANDS

(75) Inventors: Michael Kassiou, New South Wales (AU); Michelle Louise James, Menlo Park, CA (US); Christopher Andrew Luus, New South Wales (AU)

(73) Assignee: The University of Sydney, New South Wales (AU)

( * ) Notice: Subject to any disclaimer, the term of this patent is extended or adjusted under 35 U.S.C. 154(b) by 276 days.

(21) Appl. No.: 12/809,546

(22) PCT Filed: Dec. 2, 2008

(86) PCT No.: PCT/AU2008/001781
§ 371 (c)(1),
(2), (4) Date: Jun. 18, 2010

(87) PCT Pub. No.: WO2009/079683
PCT Pub. Date: Jul. 2, 2009

(65) Prior Publication Data
US 2011/0044898 A1    Feb. 24, 2011

(30) Foreign Application Priority Data

Dec. 21, 2007    (AU) ............... 2007907087

(51) Int. Cl.
*A61K 31/495* (2006.01)
(52) U.S. Cl.
USPC .......... 514/248; 514/427; 514/343; 424/1.85; 424/1.89; 424/9.1
(58) Field of Classification Search
USPC ................ 424/1.85, 1.89, 9.1; 514/221, 248, 514/343
See application file for complete search history.

(56) References Cited

U.S. PATENT DOCUMENTS 6,806,267 B1    10/2004    Williams et al.

FOREIGN PATENT DOCUMENTS

| WO | WO 03/080545 A2 | 10/2003 |
| WO | WO 2007/110437 A1 | 10/2007 |
| WO | WO-2007/134362 | * 11/2007 |
| WO | WO 2007/134362 A1 | 11/2007 |
| WO | WO 2008/022396 A1 | 2/2008 |

OTHER PUBLICATIONS

Michelle L. Tames et al., Synthesis and in vivo evaluation of a novel peripheral benzodiazepine receptor PEt radioligand, Bioorganic & Medicinal Chemsitry, 13, 6188-6194, 2005.*
M. Kassiou et al., Imporved synthesis of the peripheral benzodiazepine receptor ligand [11C]DPA-713 using '11C] methyl triflate, Applied Radiation and Isoptopes, 64, 570-573, 2006.*
International Search Report from the Australian Patent Office for International Application No. PCT/AU2008/001781, mailed Feb. 11, 2009.
Campiani, et al., "Pyrrolobenzoxazepinone Derivatives as Non-Nucleoside HIV-1 RT Inhibitors: Further Structure-Activity Relationship Studies and Identification of More Potent Broad-Spectrum HIV-1 RT Inhibitors with Antiviral Activity", J. Med. Chem, 42, pp. 4462-4470, (1999).
Greco, et al., "A Comparative Molecular Field Analysis Model for 6-Arylpyrrolo [2,1-*d*] [1,5] benzothiazepines Binding Selectively to the Mitochondrial Benzodiazepine Receptor", J. Med. Chem, 37, pp. 4100-4108, (1994).
Fiorini, et al., "Novel Ligands Specific for Mitochondrial Benzodiazepine Receptors: 6-Arylpyrrolo[2,1-*d*] [1,5] benzothiazepine Derivatives. Synthesis, Structure-Activity Relationships, and Molecular Modeling Studies", J. Med. Chem. 37, pp. 1427-1438, (1994).
F. Mattner et al., "In Vivo Evaluation of A 18F-Labelled Imidazopyridazine for the Study of the Peripheral Benzodiazepine Binding Sites Using PET," Journal of Labelled Compounds and Radiopharmaceuticals, vol. 50, No. S1, Apr. 11, 2007, Abstract, p. S76.
Sacchi et al., "Research on heterocyclic compounds, XLI. 2-Phenylimidazo[1,2-b]pyridazine-3-acetic derivatives: synthesis and anti-inflammatory activity," European Journal of Medicinal Chemistry, vol. 34, No. 11, Nov. 1, 1999, pp. 1003-1008.
Supplemental European Search Report mailed Sep. 22, 2011 for European Patent Application No. 08865479.3-2117 [EP 08865479].

* cited by examiner

*Primary Examiner* — Michael G Hartley
*Assistant Examiner* — Jagadishwar Samala
(74) *Attorney, Agent, or Firm* — Woodcock Washburn LLP

(57) ABSTRACT

The present invention relates to compounds and methods for imaging translocator protein (18 kDa) (TSPO) expression in a subject. This invention also relates to compounds and methods for the treatment of neurodegenerative disorders, inflammation or anxiety in a subject.

6 Claims, 1 Drawing Sheet

[$^{18}$F]PDAZ-FE    [$^{18}$F]PDAZ-FE + PK11195 (3mg/Kg)
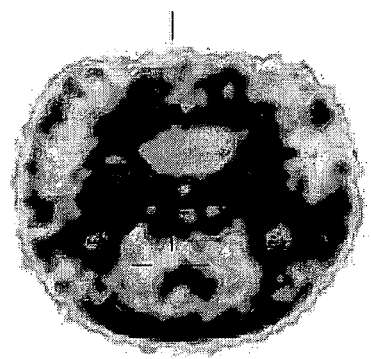 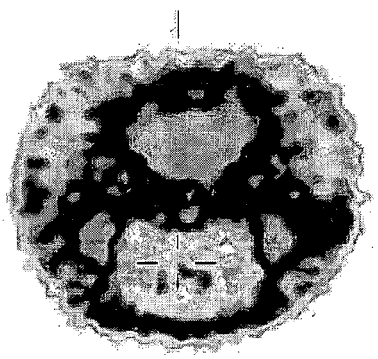
 

TRANSLOCATOR PROTEIN LIGANDS

FIELD OF THE INVENTION

The present invention relates to compounds and methods for imaging translocator protein (18 kDa) (TSPO) expression in a subject. This invention also relates to compounds and methods for the treatment of neurodegenerative disorders, inflammation or anxiety in a subject and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

The translocator protein (18 kDa) (TSPO), formerly known as the peripheral benzodiazepine receptor (PBR), can form a trimeric complex with the adenine nucleotide carrier (ANC) (30 kDa) and the voltage-dependent anion channel (VDAC) (32 kDa) to constitute the mitochondrial permeability transition pore (MPTP). The TSPO is distinguished from the central benzodiazepine receptor (CBR) by its distinct structure, physiological functions and subcellular location on the outer membrane of the mitochondria. Although the TSPO has been implicated in numerous biological processes, some aspects of its physiological role remain unclear. Studies implicate the TSPO in the rate limiting step of steroid biosynthesis, immunomodulation, porphyrin transport, calcium homeostasis, and programmed cell death.

The TSPO has been implicated in a variety of diseases, including: glioblastoma (Pappata et al., 1991 *J Nucl Med* 32:1608-10; Veenman et al., 2004 *Biochem Pharmacol.* 68(4):689-98; Levin, 2005 *Biochemistry* 44(29):9924-35), multiple sclerosis (Vowinckel et al., 1997 *J Neurosci Res* 50:345-53; Banati et al., 2000 *Brain* 123(Pt 11): 2321-37; Debruyne et al., 2003 *Eur J Neurol* 10: 257-64; Versijpt et al., 2005 *Mult Scler* 11:127-34; Chen and Guilarte, 2006 *Toxicol Sci.* 91(2):532-9), ischemic stroke (Gerhard et al., 2000 *Neuroreport;* 11:2957-60; Gerhard et al., 2005 *Neuroimage* 24:591-5; Price et al., 2006 *Stroke* 37:1749-53), herpes encephalitis (Cagnin et al., 2001 *Brain;* 124:2014-27), Parkinson's disease (Cumming et al., 2001. *Acta Neurol Scand* 103:309-15; Cicchetti et al., 2002 *Eur J Neurosci* 15:991-8; Ouchi et al., 2005 57:168-75; Gerhard et al., 2006 *Neurobiol Dis* 21:404-12; Cumming et al., 2006 *Synapse* 59:418-26), HIV (Venneti et al., 2004 *J Clin Invest* 113:981-9; Hammoud et al., 2005 *J Neurovirol* 11:346-55; Wiley et al., 2006 *J Neurovirol* 12:262-71), amyotrophic lateral sclerosis (Turner et al., 2004 *Neurobiol Dis* 15:601-9), corticobasal degeneration (Henkel et al., 2004 *Mov Disord* 19:817-21; Gerhard et al., 2004 *Mov Disord* 19:1221-6), Huntington's disease (Pavese et al., 2006 *Neurology* 66:1638-43), Cancer (Hardwick et al., 2002 *Cancer Genet Cytogenet.* 139(1):48-51; Papadopoulo V. 2003 *Ann Pharm Fr.* 61(1):30-50; Han Z., 2003 *J Recept Signal Transduct Res.* 23(2-3):225-38), Alzheimer's disease (Papadopoulo V. 2003 *Ann Pharm Fr.* 61(1): 30-50; Li et al., 2007 *Biochem Pharmaco.* 73(4):491-503), depression (Gavioli E C., 2003 *Eur J Pharmacol.* 13; 471(1): 21-6; Kita A. 2004 *Br J. Pharmacol.* 142(7):1059-72) and Cancer, auto-immune, infectious and neurodegenerative diseases (Galiegue et al., 2003 *Curr Med Chem* 10: 1563-72). It is widely acknowledged that ligands of the TSPO may be of benefit in the treatment of such diseases.

The TSPO is densely distributed in most peripheral organs including the lungs, heart and kidneys, yet it is only minimally expressed in the normal brain parenchyma. Following neuronal injury or infection, TSPO expression in the brain parenchyma is dramatically increased. In vitro autoradiography and immunohistochemistry has revealed that elevated TSPO binding in this region directly correlated with the appearance of activated microglia. Recently, in vivo positron emission tomography (PET) imaging in patients suffering from Alzheimer's disease (AD) and multiple sclerosis (MS) confirmed that TSPO binding in the brain parenchyma was confined to activated microglial cells.

Microglia are the principal immune effecter cells of the central nervous system (CNS). These macrophage-like immune cells are assumed to derive from monocytic lineage and their primary role lies in host defense and immune surveillance. They are highly sensitive to changes in their microenvironment and rapidly become activated in response to pathological events. For this reason, the TSPO is believed to be intimately associated with initial inflammatory processes in the early stages of several neurodegenerative disorders.

A number of classes of TSPO ligands have been reported over the past few decades including the benzodiazepines (diazepam and Ro 5-4864), isoquinoline carboxamides (PK 11195), indoleacetamides (FGIN-1-27), phenoxyphenyl-acetamides (DAA1106), pyrazolopyrimides (DPA-713), benzothiazepines and imidazopyridines. Some other classes have also been developed. However, a more extensive range of ligands with varying binding properties and biological activity is required to better characterise the physiological and therapeutic roles of TSPO, its exact localisation and the anticipated existence of TSPO subtypes.

The isoquinoline carboxamide [$^{11}$C](R)-PK 11195 has been used as a pharmacological probe for studying the function and expression of TSPO. A number of PET studies conducted in patients with AD, MS and multiple system atrophy (MSA) has shown that measurement of TSPO in vivo with [$^{11}$C](R)-PK 11195 is feasible in the living brain. Although [$^{11}$C](R)-PK 11195 is regarded as the most widely used PET TSPO ligand it displays a poor signal to noise ratio and has demonstrated low brain permeability which ultimately decreases its sensitivity as a marker of microglial activation.

In 1998, the phenoxyphenyl-acetamide derivative, DAA1106, was reported as a highly selective and potent ligand for the TSPO (Chaki, S.; Funakoshi, T.; Yoshikawa, R.; Okuyama, S.; Okubo, T.; Nakazato, A.; Nagamine, M.; Tomisawa, K. *European Journal of Pharmacology,* 1999, 371, 197-204). DAA1106 has been labelled with carbon-11 ($^{11}$C) and used in PET studies to evaluate its in vivo kinetics in both rodent and primate brains (Zhang M R, Kida T, Noguchi J et al. [$^{11}$C]DAA1106: radiosynthesis and in vivo binding to peripheral benzodiazepine receptors in mouse brain. *Nucl Med Biol* 2003; 30:513-519. Maeda J, Suhara T, Zhang M R et al. Novel peripheral benzodiazepine receptor ligand [$^{11}$C] DAA1106 for PET: An imaging tool for glial cells in the brain. *Synpse.* 2004; 52:283-291). The binding of [$^{11}$C] DAA1106 was shown to be four times greater than [$^{11}$C](R)-PK 11195 in the monkey occipital cortex, indicating its superior brain permeability. A fluorine-18 ($^{18}$F) analogue of this compound has also been synthesised, namely [$^{18}$F] FEDAA1106, and this analogue also displays similar binding characteristics in vivo to [$^{11}$C]DAA1106 (Zhang M R, Maeda J, Ogawa M et al. Development of a new radioligand, N-(5-fluoro-2-phenoxyphenyl)-N-(2-[$^{18}$F]fluoroethyl-5-methoxybenzyl)acetamide, for PET imaging of peripheral benzodiazepine receptor in primate brain. *J Med Chem.* 2004;

47:2228-2235. The binding of both [$^{11}$C]DAA1106 and [$^{18}$F] FEDAA1106, however, appear to be irreversible and, in fact, their slow elimination from the brain indicates that they may not have suitable kinetics for quantitative analysis.

Ryu J K et al, *Neurobiology of Disease*, 20 (2005) 550-561 reports that the TSPO ligand PK 11195 reduces microglial activation and neuronal death in quinolinic acid-injected rat stratum. The results reported in this paper suggest that inflammatory responses from activated microglia are damaging to striatal neurons and thus pharmacological targeting of TSPO in microglia is likely to protect neurons in neurological disorders.

More recently in WO 2007/134362, the present Applicant has shown 2-arylpyrazolo(1,5-a]pyrimidin-3-yl acetamide derivatives as ligands, and in particular DPA-714, specifically bind to TSPO with high affinity.

International application WO 2008/022396 discloses fluorinated ligands for targeting peripheral benzodiazepine receptors.

It would be advantageous to identify TSPO ligands with improved brain kinetics that can be used to image TSPO expression in vivo, as such ligands could be utilised to further study the cascade of biochemical events involved in the initial stages of several neurodegenerative disorders. It would also be advantageous to identify TSPO ligands with improved brain kinetics as such ligands have potential to serve as both diagnostic and therapeutic tools for neurodegenerative disorders.

It is an object of the present invention to overcome or ameliorate at least one of the disadvantages of the prior art, or to provide a useful alternative.

It is an object of the invention in its preferred form to provide compounds and methods for imaging translocator protein (18 kDa) (TSPO) expression in a subject. It is also an object of the invention in its preferred form to provide compounds and methods for the treatment of neurodegenerative disorders, inflammation or anxiety in a subject.

SUMMARY OF THE INVENTION

According to a first aspect, the present invention provides a compound of formula (III)

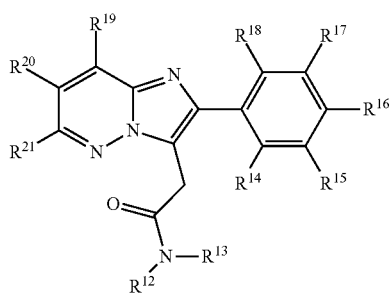

(III)

wherein
$R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
or $R^{12}$ and $R^{13}$, together with the nitrogen to which they are attached, form an optionally substituted heterocyclic ring having between 3 and 7 ring members;

$R^{14}$, $R^{15}$, $R^{16}$, $R^{17}$ and $R^{18}$ are each independently H, halo, OH, NO$_2$, optionally substituted alkyl, optionally substituted alkoxy, optionally substituted alkenyl, optionally substituted alkynyl, optionally substituted aryl, optionally substituted heteroaryl, optionally substituted NHC$_{1-6}$ alkyl, optionally substituted SC$_{1-6}$ alkyl, COOR$^{22}$, (CH$_2$)$_n$OR$^{22}$ or an optionally substituted polyether;

$R^{19}$ and $R^{21}$ are each independently halo, OH, NO$_2$, optionally substituted alkyl, optionally substituted alkoxy, optionally substituted alkenyl, optionally substituted alkynyl, optionally substituted aryl, optionally substituted heteroaryl, optionally substituted NHC$_{1-6}$ alkyl, optionally substituted SC$_{1-6}$ alkyl, COOR$^{22}$, (CH$_2$)$_n$OR$^{22}$ or an optionally substituted polyether;

$R^{20}$ is H, halo, OH, NO$_2$, optionally substituted alkyl, optionally substituted alkoxy, optionally substituted alkenyl, optionally substituted alkynyl, optionally substituted aryl, optionally substituted heteroaryl, optionally substituted NHC$_{1-6}$ alkyl, optionally substituted SC$_{1-6}$ alkyl, COOR$^{22}$, (CH$_2$)$_n$OR$^{22}$ or an optionally substituted polyether;

$R^{22}$ is optionally substituted alkyl; and
n is an integer from 1 to 6;
or a salt or solvate thereof.

Preferably $R^{20}$ is H.

$R^{19}$ and $R^{21}$ preferably are each independently $C_{1-6}$ alkyl. More preferably $R^{19}$ and $R^{21}$ are each independently methyl.

Preferably $R^{14}$, $R^{15}$, $R^{16}$, $R^{17}$ and $R^{18}$ are each independently H, halo, OH, NO$_2$, optionally substituted $C_{1-6}$ alkyl, optionally substituted OC$_{1-6}$ alkyl or optionally substituted aryl. More preferably $R^{14}$, $R^{15}$, $R^{17}$ and $R^{18}$ are H.

Even more preferably $R^{16}$ is halo, OH, optionally substituted $C_{1-6}$ alkyl or optionally substituted OC$_{1-6}$ alkyl.

Preferably $R^{12}$ and $R^{13}$ are each independently a $C_{1-6}$ alkyl. More preferably $R^{12}$ and $R^{13}$ are each independently ethyl.

Preferably $R^{16}$ is OCH$_3$, CH$_3$, Cl, Br, F, OH, OCH$_2$CH$_2$OTs or OCH$_2$CH$_2$F.

In certain embodiments, preferably $R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
or $R^{12}$ and $R^{13}$, together with the nitrogen to which they are attached, form an optionally substituted heterocyclic ring having between 3 and 7 ring members;

$R^{14}$, $R^{15}$, $R^{16}$, $R^{17}$ and $R^{18}$ are each independently H, halo, OH, NO$_2$, optionally substituted alkyl, optionally substituted alkoxy, optionally substituted alkenyl, optionally substituted alkynyl, optionally substituted aryl, optionally substituted heteroaryl, optionally substituted NHC$_{1-6}$ alkyl, optionally substituted SC$_{1-6}$ alkyl, COOR$^{22}$, (CH$_2$)$_n$OR$^{22}$ or an optionally substituted polyether;

$R^{19}$ and $R^{21}$ are each independently halo, OH, NO$_2$, optionally substituted alkyl, optionally substituted alkoxy, optionally substituted alkenyl, optionally substituted alkynyl, optionally substituted aryl, optionally substituted heteroaryl, optionally substituted NHC$_{1-6}$ alkyl, optionally substituted SC$_{1-6}$ alkyl, COOR$^{22}$, (CH$_2$)$_n$OR$^{22}$ or an optionally substituted polyether;

$R^{20}$ is H;
$R^{22}$ is optionally substituted alkyl; and
n is an integer from 1 to 6.

Preferably $R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
  or $R^{12}$ and $R^{13}$, together with the nitrogen to which they are attached, form an optionally substituted heterocyclic ring having between 3 and 7 ring members;
$R^{14}$, $R^{15}$, $R^{16}$, $R^{17}$ and $R^{18}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{22}$, $(CH_2)_nOR^{22}$ or an optionally substituted polyether;
$R^{19}$ and $R^{21}$ are each independently $C_{1-6}$ alkyl;
$R^{20}$ is H;
$R^{22}$ is optionally substituted alkyl; and
n is an integer from 1 to 6.

Preferably $R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
  or $R^{12}$ and $R^{13}$, together with the nitrogen to which they are attached, form an optionally substituted heterocyclic ring having between 3 and 7 ring members;
$R^{14}$, $R^{15}$, $R^{16}$, $R^{17}$ and $R^{18}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{22}$, $(CH_2)_nOR^{22}$ or an optionally substituted polyether;
$R^{19}$ and $R^{21}$ are each independently methyl;
$R^{20}$ is H;
$R^{22}$ is optionally substituted alkyl; and
n is an integer from 1 to 6.

Preferably $R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
  or $R^{12}$ and $R^{13}$, together with the nitrogen to which they are attached, form an optionally substituted heterocyclic ring having between 3 and 7 ring members;
$R^{14}$, $R^{15}$, $R^{16}$, $R^{17}$ and $R^{18}$ are each independently H, halo, OH, $NO_2$, optionally substituted $C_{1-6}$ alkyl, optionally substituted $OC_{1-6}$ alkyl or optionally substituted aryl;
$R^{19}$ and $R^{21}$ are each independently methyl; and
$R^{20}$ is H.

Preferably $R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
  or $R^{12}$ and $R^{13}$, together with the nitrogen to which they are attached, form an optionally substituted heterocyclic ring having between 3 and 7 ring members;
$R^{14}$, $R^{15}$, $R^{17}$ and $R^{18}$ are H;
$R^{16}$ is H, halo, OH, $NO_2$, optionally substituted $C_{1-6}$ alkyl, optionally substituted $OC_{1-6}$ alkyl or optionally substituted aryl;
$R^{19}$ and $R^{21}$ are each independently methyl; and
$R^{20}$ is H.

Preferably $R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
  or $R^{12}$ and $R^{13}$, together with the nitrogen to which they are attached, form an optionally substituted heterocyclic ring having between 3 and 7 ring members;
$R^{14}$, $R^{15}$, $R^{17}$ and $R^{18}$ are H;
$R^{16}$ is halo, OH, optionally substituted $C_{1-6}$ alkyl or optionally substituted $OC_{1-6}$ alkyl;
$R^{19}$ and $R^{21}$ are each independently methyl; and
$R^{20}$ is H.

Preferably $R^{12}$ and $R^{13}$ are each independently a $C_{1-6}$ alkyl;
$R^{14}$, $R^{15}$, $R^{17}$ and $R^{18}$ are H;
$R^{16}$ is halo, OH, optionally substituted $C_{1-6}$ alkyl or optionally substituted $OC_{1-6}$ alkyl;
$R^{19}$ and $R^{21}$ are each independently methyl; and
$R^{20}$ is H.

More preferably $R^{12}$ and $R^{13}$ are each independently ethyl;
$R^{14}$, $R^{15}$, $R^{17}$ and $R^{18}$ are H;
$R^{16}$ is halo, OH, optionally substituted $C_{1-6}$ alkyl or optionally substituted $OC_{1-6}$ alkyl;
$R^{19}$ and $R^{21}$ are each independently methyl; and
$R^{20}$ is H.

Preferably the compound according to first aspect is selected from the group consisting of:

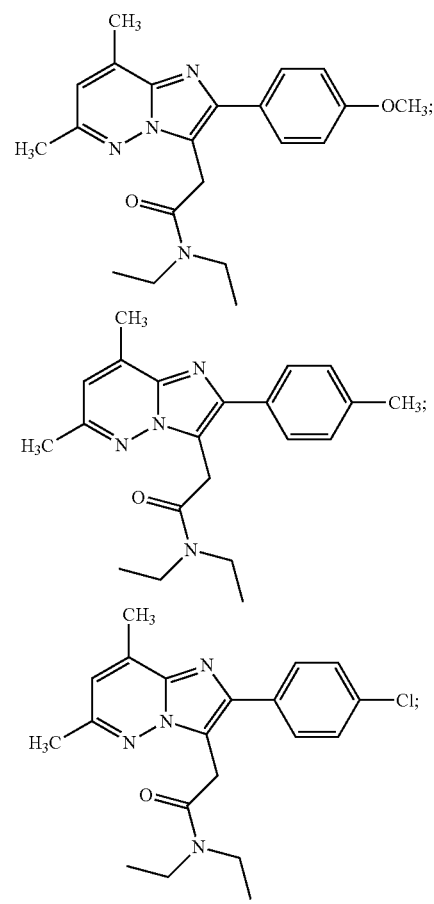

-continued

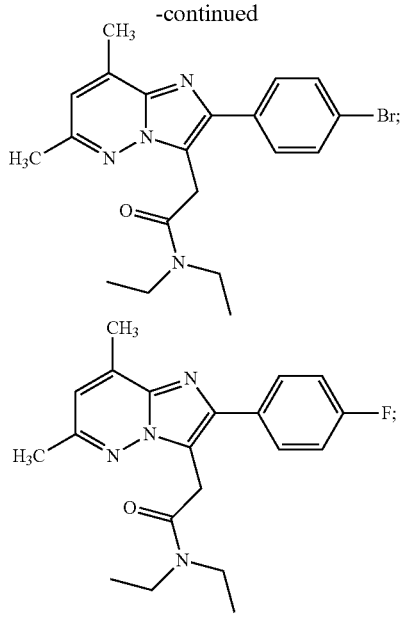

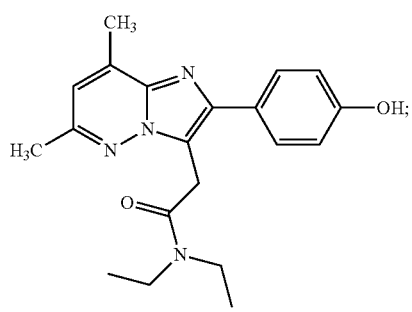

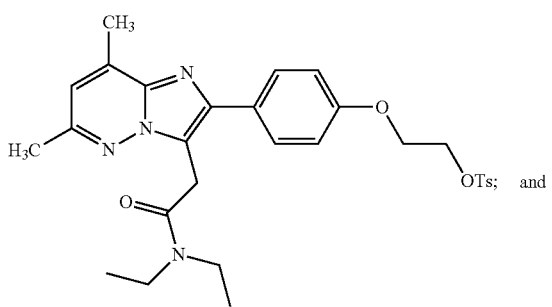

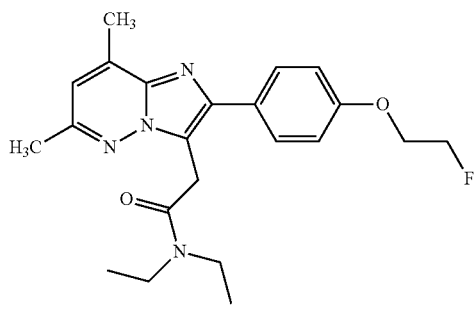

or a salt or solvate thereof.

According to a second aspect, the present invention provides a compound of formula (IV)

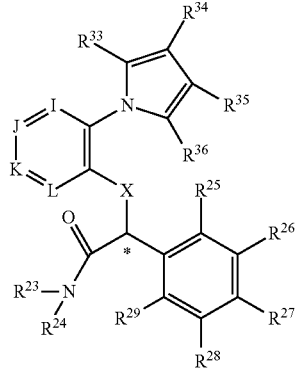

wherein
$R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;
or $R^{23}$ and $R^{24}$, together with the nitrogen to which they are attached, form an optionally substituted heterocyclic ring having between 3 and 7 ring members;
$R^{25}$, $R^{26}$, $R^{27}$, $R^{28}$ and $R^{29}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;
$R^{30}$ is optionally substituted alkyl;
n is an integer from 1 to 6;
X is selected from the group consisting of O, NH and S;
I, J, K and L are each independently $CR^{31}$ or N;
$R^{31}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether; and
$R^{33}$, $R^{34}$, $R^{35}$ and $R^{36}$ are each independently H, halo, OH, $NO_2$, optionally substituted alkyl, optionally substituted alkoxy, optionally substituted alkenyl, optionally substituted alkynyl, optionally substituted aryl or optionally substituted heteroaryl; or a salt or solvate thereof.

Preferably X is O.

Preferably I is N and J, K, L are $CR^{31}$. Preferably I, J, K and L are $CR^{31}$. Preferably each $R^{31}$ is independently H, halo or an optionally substituted alkyl.

$R^{25}$, $R^{26}$, $R^{28}$ and $R^{29}$ are preferably H. Preferably $R^{33}$, $R^{34}$, $R^{35}$ and $R^{36}$ are H.

$R^{27}$ is preferably halo, OH, $NO_2$, optionally substituted alkyl, optionally substituted alkoxy or optionally substituted aryl. More preferably $R^{27}$ is OH, $CH_3$, $OCH_3$, $NO_2$, F, Cl or naphthyl. Most preferably $R^{27}$ is F, Cl or $OCH_3$.

$R^{23}$ and $R^{24}$ are preferably each independently a $C_{1-6}$ alkyl. More preferably $R^{23}$ and $R^{24}$ are each independently selected from the group consisting of ethyl, propyl and i-propyl.

Preferably the compound according to the second aspect is the (R)-enantiomer.

In certain embodiments, preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{25}$, $R^{26}$, $R^{27}$, $R^{28}$ and $R^{29}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;

$R^{30}$ is optionally substituted alkyl;

n is an integer from 1 to 6;

X is O;

I, J, K and L are each independently $CR^{31}$ or N;

$R^{31}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether; and $R^{33}$, $R^{34}$, $R^{35}$ and $R^{36}$ are each independently H, halo, OH, $NO_2$, optionally substituted alkyl, optionally substituted alkoxy, optionally substituted alkenyl, optionally substituted alkynyl, optionally substituted aryl or optionally substituted heteroaryl.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{25}$, $R^{26}$, $R^{27}$, $R^{28}$ and $R^{29}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;

$R^{30}$ is optionally substituted alkyl;

n is an integer from 1 to 6;

X is O;

I is N and J, K, L are $CR^{31}$;

$R^{31}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether; and $R^{33}$, $R^{34}$, $R^{35}$ and $R^{36}$ are each independently H, halo, OH, $NO_2$, optionally substituted alkyl, optionally substituted alkoxy, optionally substituted alkenyl, optionally substituted alkynyl, optionally substituted aryl or optionally substituted heteroaryl.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{25}$, $R^{26}$, $R^{27}$, $R^{28}$ and $R^{29}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;

$R^{30}$ is optionally substituted alkyl;

n is an integer from 1 to 6;

X is O;

I, J, K and L are $CR^{31}$;

$R^{31}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether; and $R^{33}$, $R^{34}$, $R^{35}$ and $R^{36}$ are each independently H, halo, OH, $NO_2$, optionally substituted alkyl, optionally substituted alkoxy, optionally substituted alkenyl, optionally substituted alkynyl, optionally substituted aryl or optionally substituted heteroaryl.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{25}$, $R^{26}$, $R^{27}$, $R^{28}$ and $R^{29}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;

$R^{30}$ is optionally substituted alkyl;

n is an integer from 1 to 6;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are each independently H, halo, OH, $NO_2$, optionally substituted alkyl, optionally substituted alkoxy, optionally substituted alkenyl, optionally substituted alkynyl, optionally substituted aryl or optionally substituted heteroaryl.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{27}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;

$R^{25}$, $R^{26}$, $R^{28}$ and $R^{29}$ are H;

$R^{30}$ is optionally substituted alkyl;

n is an integer from 1 to 6;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are each independently H, halo, OH, $NO_2$, optionally substituted alkyl, optionally substituted alkoxy, optionally substituted alkenyl, optionally substituted alkynyl, optionally substituted aryl or optionally substituted heteroaryl.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{27}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;

$R^{25}$, $R^{26}$, $R^{28}$ and $R^{29}$ are H;

$R^{30}$ is optionally substituted alkyl;

n is an integer from 1 to 6;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are H.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{27}$ is halo, OH, $NO_2$, optionally substituted alkyl, optionally substituted alkoxy or optionally substituted aryl;

$R^{25}$, $R^{26}$, $R^{28}$ and $R^{29}$ are H;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are H.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{27}$ is OH, $CH_3$, $OCH_3$, $NO_2$, F, Cl or naphthyl;

$R^{25}$, $R^{26}$, $R^{28}$ and $R^{29}$ are H;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are H.

Preferably $R^{23}$ and $R^{24}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{23}$ and $R^{24}$, together with the nitrogen to which they are attached, form an optionally substituted heterocyclic ring having between 3 and 7 ring members;

$R^{27}$ is F, Cl or $OCH_3$;

$R^{25}$, $R^{26}$, $R^{28}$ and $R^{29}$ are H;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are H.

Preferably $R^{23}$ and $R^{24}$ are each independently a $C_{1-6}$ alkyl;

$R^{27}$ is F, Cl or $OCH_3$;

$R^{25}$, $R^{26}$, $R^{28}$ and $R^{29}$ are H;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are H.

More preferably $R^{23}$ and $R^{24}$ are each independently selected from the group consisting of ethyl, propyl and i-propyl;

$R^{27}$ is F, Cl or $OCH_3$;

$R^{25}$, $R^{26}$, $R^{28}$ and $R^{29}$ are H;

X is O;

I, J, K and L are $CR^{31}$ or I is N and J, K, L are $CR^{31}$;

$R^{31}$ is independently H, halo or an optionally substituted alkyl; and $R^{33}$, $R^{34}$, $R^{35}$ and $R^{36}$ are H.

Preferably the compound according to second aspect is selected from the group consisting of:

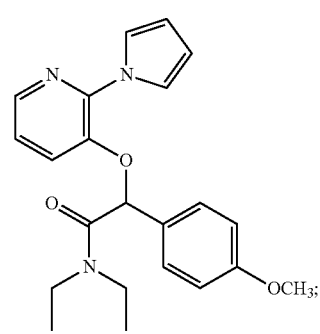

-continued

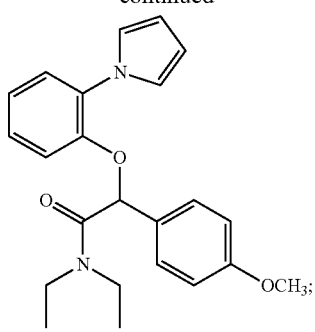

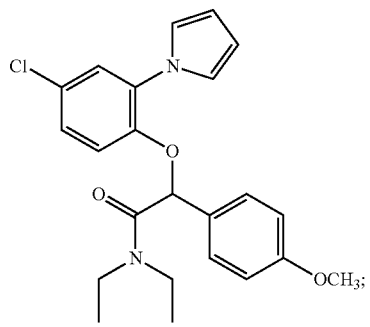

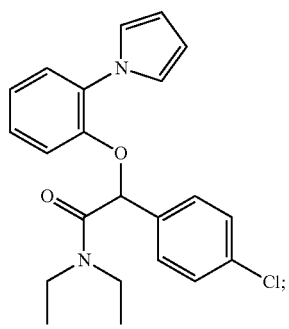

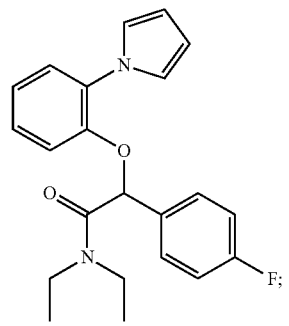

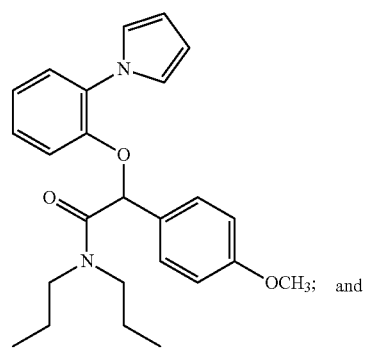 and

-continued

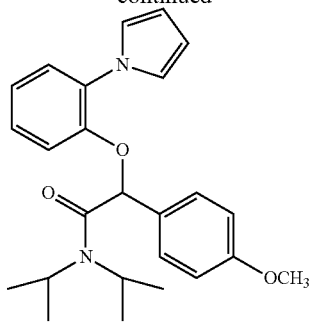

or a salt or solvate thereof.

Preferably the compound according to second aspect is the (R)-enantiomer.

The skilled address would appreciate that I, J, K and L are each independently N or $CR^{31}$ in any combination. Preferably I, J, K, and L when taken together contain 0, 1, 2, 3 or 4 N atoms in any combination. More preferably I, J, K, and L when taken together contain 0, 1, 2 or 3 N atoms in any combination. Even more preferably I, J, K, and L when taken together contain 0, 1 or 2 N atoms in any combination. Most preferably I, J, K, and L when taken together contain 0 or 1 N atom in any combination i.e. Preferably J is N, and I, K and L are each independently $CR^{31}$. Preferably K is N, and I, J and L are each independently $CR^{31}$. Preferably L is N, and I, J and K are each independently $CR^{31}$. Most preferably I is N, and J, K and L are each independently $CR^{31}$. Equally preferably I, J, K and L are $CR^{31}$. Even more preferably I, J, K and L are CH. Preferably I, K, and L are CH and J is $CR^{31}$, wherein $R^{31}$ is halo. I, J, K and L together with the two carbon atoms to which they are attached preferably form an optionally substituted benzene or pyridine ring. Preferably the ring is optionally substituted with halo. More preferably the halo is chloro.

According to a third aspect, the present invention provides a compound of formula (V) for use as an intermediate in the production of a compound of formula (IV)

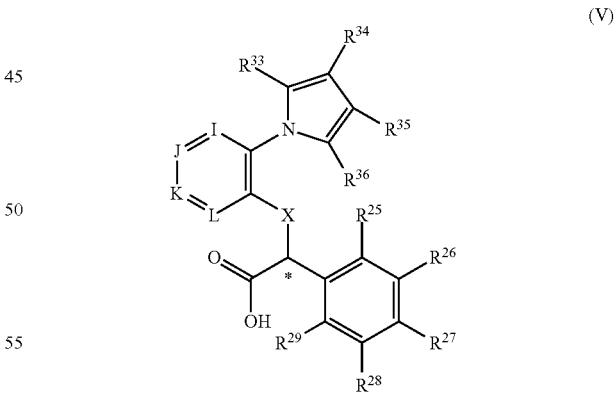

wherein $R^{25}$, $R^{26}$, $R^{27}$, $R^{28}$ and $R^{29}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether;

$R^{30}$ is optionally substituted alkyl;

n is an integer from 1 to 6;

X is selected from the group consisting of O, NH and S;

I, J, K and L are each independently $CR^{31}$ or N;

$R^{31}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{30}$, $(CH_2)_nOR^{30}$ or an optionally substituted polyether; and $R^{33}$, $R^{34}$, $R^{35}$ and $R^{36}$ are each independently H, halo, OH, $NO_2$, optionally substituted alkyl, optionally substituted alkoxy, optionally substituted alkenyl, optionally substituted alkynyl, optionally substituted aryl or optionally substituted heteroaryl;

or a salt or solvate thereof;

provided that when I is N, $R^{27}$ is not methyl.

Preferably X is O.

Preferably I is N and J, K, L are $CR^{31}$. Preferably I, J, K and L are $CR^{31}$. Preferably each $R^{31}$ is independently H, halo or an optionally substituted alkyl.

$R^{25}$, $R^{26}$, $R^{28}$ and $R^{29}$ are preferably H. Preferably $R^{33}$, $R^{34}$, $R^{35}$ and $R^{36}$ are H.

$R^{27}$ is preferably halo, OH, $NO_2$, optionally substituted alkyl, optionally substituted alkoxy or optionally substituted aryl. More preferably $R^{27}$ is OH, $CH_3$, $OCH_3$, $NO_2$, F, Cl or naphthyl. Most preferably $R^{27}$ is F, Cl or $OCH_3$.

Preferably the compound according to the third aspect is the (R)-enantiomer.

Preferably the compound according to third aspect is selected from the group consisting of:

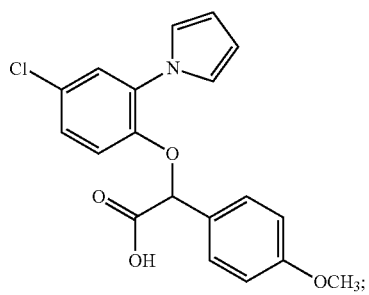

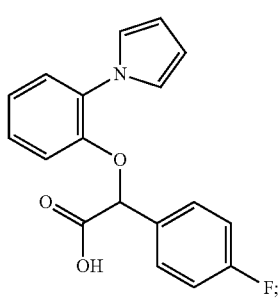

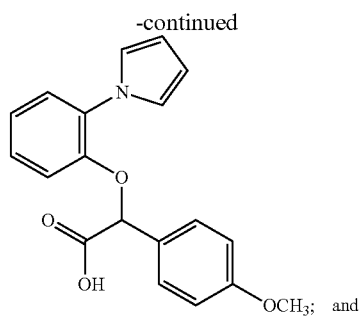

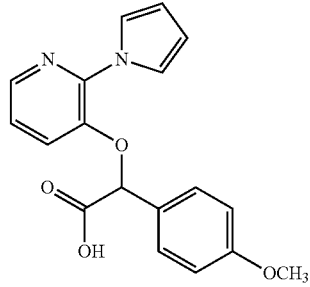

or a salt or solvate thereof.

According to a fourth aspect, the present invention provides a compound according to the first aspect or the second aspect radiolabelled with a radioisotope. Preferably said radioisotope is selected from $^{18}F$, $^{123}I$, $^{76}Br$, $^{124}I$ and $^{75}Br$. More preferably the radioisotope is $^{18}F$.

According to a fifth aspect, the present invention provides a pharmaceutical composition comprising a compound according to the first, second or fourth aspects, or a pharmaceutically acceptable salt thereof, and a pharmaceutically acceptable carrier.

According to a sixth aspect, the present invention provides a method of diagnosing a disorder in a subject comprising administering to a subject a compound according to any one of the first, second or fourth aspects. Preferably the method comprises imaging translocator protein (18 kDa) (TSPO) in the subject. More preferably the method comprises obtaining an image indicating the location of the protein.

Preferably when the compound is radiolabelled with a radioisotope, the radioisotope is selected from the group consisting of $^{18}F$, $^{123}I$, $^{76}Br$, $^{124}I$ and $^{75}Br$. More preferably the compound is radiolabelled with $^{18}F$, $^{76}Br$, $^{124}I$ or $^{75}Br$ and the image is obtained by positron emission tomography (PET) imaging. Preferably the compound is radiolabelled with $^{123}I$ and the image is obtained by SPECT imaging. The image preferably is obtained to assess the extent of TSPO binding of the compound or salt thereof in the brain parenchyma of the subject.

The disorder is preferably a neurodegenerative disorder, inflammation or anxiety.

Preferably the disorder is selected from the group consisting of: Alzheimer's disease, Parkinson's disease, Huntington's disease, multiple sclerosis, multiple system atrophy, epilepsy, encephalopathy, stroke, brain tumour, anxiety, stress, emotional disturbances or cognitive impairment, glioblastoma, ischemic stroke, herpes encephalitis, HIV, amyotrophic lateral sclerosis, corticobasal degeneration, cancer, depression, an auto-immune disease and an infectious disease. The subject is preferably a human.

According to a seventh aspect, the present invention provides use of a compound according to the first, second or fourth aspects in the manufacture of an agent for diagnosing a disorder in a subject.

Preferably diagnosing the disorder comprises imaging translocator protein (18 kDa) in the subject. Preferably when the compound is radiolabelled with a radioisotope, the radioisotope is selected from the group consisting of $^{18}$F, $^{123}$I, $^{76}$Br, $^{124}$I and $^{75}$Br. The compound is preferably radiolabelled with $^{18}$F, $^{76}$Br, $^{124}$I or $^{75}$Br and a translocator protein image is obtained by positron emission tomography (PET) imaging. The compound is preferably radiolabelled with $^{123}$I and a translocator protein image is obtained by SPECT imaging.

The disorder is preferably a neurodegenerative disorder, inflammation or anxiety.

Preferably the disorder is selected from the group consisting of: Alzheimer's disease, Parkinson's disease, Huntington's disease, multiple sclerosis, multiple system atrophy, epilepsy, encephalopathy, stroke, brain tumour, anxiety, stress, emotional disturbances or cognitive impairment, glioblastoma, ischemic stroke, herpes encephalitis, HIV, amyotrophic lateral sclerosis, corticobasal degeneration, cancer, depression, an auto-immune disease and an infectious disease.

According to an eighth aspect, the present invention provides a process for preparing a compound of formula (III), or a salt or solvate thereof, the process comprising reacting a compound of formula (VII) with a compound of formula (VIII)

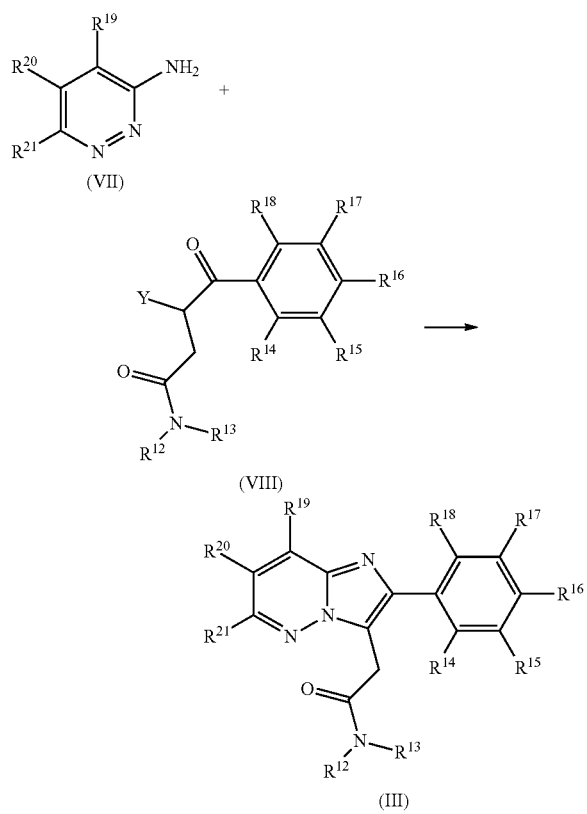

wherein $R^{12}$, $R^{13}$, $R^{14}$, $R^{15}$, $R^{16}$, $R^{17}$, $R^{18}$, $R^{19}$, $R^{20}$ and $R^{21}$ are defined according to the first aspect and wherein Y is a leaving group that reacts with VII. Preferably Y is halo.

According to a ninth aspect, the present invention provides a compound of formula (III) when prepared by the process of the eight aspect.

According to a tenth aspect, the present invention provides a process for preparing a compound of formula (IV), or a salt or solvate thereof, the process comprising reacting a compound of formula (V) with a compound of formula (VI)

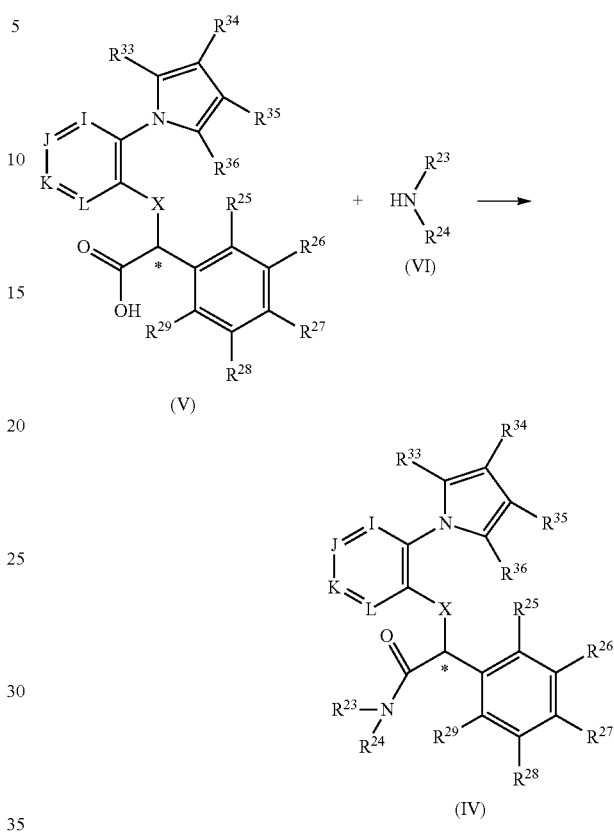

wherein I, J, K, L, X, $R^{23}$, $R^{24}$, $R^{25}$, $R^{26}$, $R^{27}$, $R^{28}$, $R^{29}$, $R^{33}$, $R^{34}$, $R^{35}$ and $R^{36}$ are defined according to the second aspect.

According to an eleventh aspect, the present invention provides a compound of formula (IV) when produced by the process of the tenth aspect.

According to a twelfth aspect, the present invention provides a compound according to the first, second or fourth aspects capable of eliciting a response when bound to a TSPO receptor.

According to a thirteenth aspect, the present invention provides use of a compound according to the first, second or fourth aspects in the manufacture of a medicament for the treatment of a disorder in a subject. Preferably the disorder is characterised by an abnormal density of TSPO receptors in a mammal. The disorder is preferably a neurodegenerative disorder, inflammation or anxiety. Preferably the disorder is selected from the group consisting of: Alzheimer's disease, Parkinson's disease, Huntington's disease, multiple sclerosis, multiple system atrophy, epilepsy, encephalopathy, stroke, brain tumour, anxiety, stress, emotional disturbances or cognitive impairment, glioblastoma, ischemic stroke, herpes encephalitis, HIV, amyotrophic lateral sclerosis, corticobasal degeneration, cancer, depression, an auto-immune disease and an infectious disease.

According to a fourteenth aspect, the present invention provides a method of treating a disorder in a subject comprising administering to the subject a compound according to the first, second or fourth aspects. Preferably the disorder is characterised by an abnormal density of TSPO receptors in a mammal. The disorder preferably is a neurodegenerative disorder, inflammation or anxiety in a subject.

Preferably the disorder is selected from the group consisting of: Alzheimer's disease, Parkinson's disease, Huntington's disease, multiple sclerosis, multiple system atrophy, epilepsy, encephalopathy, stroke, brain tumour, anxiety, stress, emotional disturbances or cognitive impairment, glioblastoma, ischemic stroke, herpes encephalitis, HIV, amyotrophic lateral sclerosis, corticobasal degeneration, cancer, depression, auto-immune and infectious diseases.

BRIEF DESCRIPTION OF THE DRAWING

A preferred embodiment of the invention will now be described, by way of example only, with reference to the accompanying figure in which:

FIG. 1 is a MicroPET image taken of a rat administered with [$^{18}$F]PDAZ-FE, and of a rat administered with [$^{18}$F] PDAZ-FE which has been pre-treated with PK 11195, shown in cross-section (top) and partly cut away longitudinal section (bottom) with cross hairs in the brain.

DETAILED DESCRIPTION OF THE INVENTION

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

As used herein, the term "alkyl" refers to a straight chain, branched or mono- or poly-cyclic alkyl. Typically, the alkyl is a $C_1$ to $C_{10}$ alkyl, for example, an alkyl group having from 1 to 10 carbon atoms e.g. 1, 2, 3, 4, 5, 6, 7, 8, 9 or 10 carbon atoms. The alkyl group may have from 1 to 2, 1 to 4, 1 to 6, 1 to 8, 1 to 10, 2 to 4, 2 to 6, 2 to 8, 2 to 10, 4 to 6, 4 to 8, 4 to 10, 6 to 8, 6 to 10 or 8 to 10 carbon atoms. Preferably the alkyl group is a $C_1$ to $C_6$ alkyl.

Examples of straight chain and branched alkyl include methyl, ethyl, propyl, isopropyl, butyl, isobutyl, sec-butyl, tert-butyl, pentyl, isopentyl, sec-pentyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl and 1,1,2-trimethylpropyl.

Examples of cyclic alkyl include cyclopropyl, cyclobutyl, cyclopentyl and cyclohexyl.

As used herein, the term "alkoxy" refers to a group of the formula Oalkyl. Examples of alkoxy include methoxy, ethoxy, propoxy and butoxy. Typically, the alkyoxy is a $C_1$ to $C_{30}$ alkoxy, for example, a $C_1$ to $C_{10}$ alkoxy, i.e. an alkoxy group having from 1 to 10 carbon atoms e.g. 1, 2, 3, 4, 5, 6, 7, 8, 9 or 10 carbon atoms. The alkoxy group may have from 1 to 2, 1 to 4, 1 to 6, 1 to 8, 1 to 10, 2 to 4, 2 to 6, 2 to 8, 2 to 10, 4 to 6, 4 to 8, 4 to 10, 6 to 8, 6 to 10 or 8 to 10 carbon atoms. More preferably the alkoxy is a $C_1$ to $C_6$ alkoxy.

As used herein, the term "alkenyl" refers to a straight chain, branched or cyclic alkenyl. Typically, the alkenyl is a $C_2$ to $C_{10}$ alkenyl, for example, an alkenyl group having from 2 to 10 carbon atoms e.g. 2, 3, 4, 5, 6, 7, 8, 9 or 10 carbon atoms. The alkenyl group may have from 2 to 4, 2 to 6, 2 to 8, 2 to 10, 4 to 6, 4 to 8, 4 to 10, 6 to 8, 6 to 10 or 8 to 10 carbon atoms. Preferably the alkenyl group is a $C_2$ to $C_6$ alkenyl. Examples of alkenyl include vinyl, allyl, 1-methylvinyl, butenyl, isobutenyl, 3-methyl-2-butenyl, 1-pentenyl, cyclopentenyl, 1-methylcyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

As used herein, the term "alkynyl" refers to a straight chain, branched or cyclic alkynyl. Typically, the alkynyl is a $C_2$ to $C_{10}$ alkynyl, for example, an alkynyl group having from 2 to 10 carbon atoms e.g. 2, 3, 4, 5, 6, 7, 8, 9 or 10 carbon atoms. The alkynyl group may have from 2 to 4, 2 to 6, 2 to 8, 2 to 10, 4 to 6, 4 to 8, 4 to 10, 6 to 8, 6 to 10 or 8 to 10 carbon atoms. Preferably the alkynyl group is a $C_2$ to $C_6$ alkynyl.

As used herein, the term "aryl" refers to a radical of a single, polynuclear, conjugated or fused aromatic hydrocarbon or aromatic heterocyclic ring system. Preferably the aryl group has from 4 to 20 carbon atoms. e.g. 4, 5, 6, 7, 8, 9, 10, 11, 12, 13, 14, 15, 16, 17, 18, 19, or 20 carbon atoms. The aryl group may have from 4 to 6, 4 to 8, 4 to 10, 4 to 12, 4 to 14, 4 to 16, 4 to 18, 4 to 20, 6 to 8, 6 to 10, 6 to 12, 6 to 14, 6 to 16, 6 to 18, 6 to 20, 8 to 10, 8 to 12, 8 to 14, 8 to 16, 8 to 18, 8 to 20, 10 to 12, 10 to 14, 10 to 16, 10 to 18, 10 to 20, 12 to 14, 12 to 16, 12 to 18 12 to 20, 14 to 16, 14 to 18, 14 to 20, 16 to 18, 16 to 20 or 18 to 20 carbon atoms. Preferably, the aryl is a $C_6$ to $C_{12}$ aryl. Examples of aryl include, although are not limited to phenyl, biphenyl, naphthyl, tetrahydronaphthyl, indenyl, azulenyl, phenanthryl, pyrenyl and the like. Any available position of the aromatic residue can be used for attachment to the remainder of the molecule of formula (III), (IV) or (V).

When the aryl comprises a heterocyclic aromatic ring system, the heterocyclic ring system may contain 1 to 4 heteroatoms independently selected from N, O and S. An aryl containing a heteroatom in the aromatic ring system is referred to as a "heteroaryl".

As used herein, the term "heteroaryl" refers to single, polynuclear, conjugated and fused aromatic radicals having between 6 and 20 ring atoms, wherein 1 to 6, or 1 to 5, or 1 to 4, or 1 to 3, or 1 or 2 of these rings atoms are heteroatoms independently selected from the group consisting of: N, NH, O and S. The heteroaryl group may have from 4 to 6, 4 to 8, 4 to 10, 4 to 12, 4 to 14, 4 to 16, 4 to 18, 6 to 10, 6 to 12, 6 to 14, 6 to 16 or 6 to 18 carbon atoms. The heteroaryl group may have 1 to 2, 1 to 3, 1 to 4, 1 to 5 or 1 to 6 heteroatoms. The hetero atoms may be independently selected from the group consisting of: N and NH, N and O, NH and O, N and S, NH and S and S and O. Examples of such heteroaryl groups include but are not limited to pyridyl, thienyl, furyl, pyrryl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Any available position of the heteroaromatic residue can be used for attachment to the remainder of the molecule of formula (III), (IV) or (V). Nitrogen-containing heteroaryl groups may be substituted at nitrogen with an oxygen atom to form an N-oxide. Sulfur-containing heteroaryl groups may be substituted at sulfur with one or two oxygen atoms to form a sulfoxide or a sulfone respectively.

As used herein, the term "halo" and "halogen" refer to a halogen radical, e.g. fluoro, chloro, bromo or iodo.

As used herein, the term polyether means a radical with more than one ether group. The polyether may, for example, be a group of the formula —$(O(CH_2)_a)_b(CH_2)_cCH_3$, where a is 1, 2 or 3, b is 2, 3, 4 or 5, and c is 0, 1, 2, 3, 4 or 5, optionally substituted with halo.

Where n is an integer, the integer is preferably from 1 to 20, more preferably from 1 to 10, even more preferably from 1 to 6. For example, n is 1, 2, 3, 4, 5 or 6.

As used herein, reference to a group "optionally substituted" means the group may be substituted with one or more substituents. For example, in certain embodiments a group may be optionally substituted with one or more alkyl, alkoxy, alkenyl, alkynyl, aryl or heteroaryl groups. More preferably the group may be optionally substituted with a substituent selected from the group consisting of halo, $C_1$-$C_{10}$ alkyl and $O(C_1$-$C_{10}$ alkyl), wherein the $C_1$-$C_{10}$ alkyl group is optionally substituted with one or more halo radicals. Preferably the halo is fluoro. In certain embodiments a group may be optionally substituted with OTs. Even more preferably the group may be optionally substituted with one or more fluoro radicals. The person skilled in the art would readily appreciate that a compound of formula (III) or formula (IV) may be fluorinated in any position for subsequent radiolabelling.

In the framework of this application, a compound according to the invention is inherently intended to comprise all stereochemically isomeric forms thereof. The term "stereochemically isomeric form" as used herein defines all the possible stereochemically isomeric forms that a compound of Formulae (III), (IV) or (V) may possess. Unless otherwise mentioned or indicated, the chemical designation of a compound denotes the mixture of all possible stereochemically isomeric forms, said mixtures containing all diastereomers and enantiomers of the basic molecular structure. More in particular, stereogenic centres may have the R- or S-configuration; substituents on bivalent cyclic (partially) saturated radicals may have either the cis- or trans-configuration. Compounds encompassing double bonds can have an E or Z-stereochemistry at said double bond. Hence, all stereochemically isomeric forms of a compound of Formulae (III), (IV) or (V) are intended to be embraced within the scope of this invention. As used herein, the notation "*" shall denote the presence of a stereogenic centre.

The present inventors have surprisingly found that the compounds of formula (III) and (IV) radiolabelled with a radioisotope are selective TSPO ligands, and may be used as accurate in vivo markers of TSPO and therefore microglial activation. These radiolabelled compounds may therefore be used to study neuropathological events in a number of neurodegenerative disorders, and may be used as a tool for diagnosis of such disorders and for monitoring the progression of such disorders.

The inventors have found that compounds of formula (III) having 6,8-dimethyl substitution are particularly selective TSPO ligands. That is compounds of formula (III) wherein $R^{19}$ and $R^{21}$ are methyl and $R^{20}$ is H show high binding affinity to TSPO.

The radioisotope can be selected from any suitable radioisotope known to the skilled addressee and include for example radioisotopes listed in the Handbook of Radiopharmaceuticals, Radiochemistry Applications, ed. Michael Welsch and Carol S. Redvanly, John Wiley & Sons Ltd 2003; and PET Chemistry, The Driving Force for Molecular Imaging. Ed. P.A. Schubiger, L. Lehmann, M. Friebe, Springer 2007. Radioisotopes include, although are not limited to, $^{18}$F, $^{123}$I, $^{76}$Br, $^{124}$I and $^{75}$Br and $^{11}$C.

As used herein, by a compound of formula (III) or (IV) "radiolabelled" with $^{18}$F, $^{123}$I, $^{76}$Br, $^{124}$I and $^{75}$Br, it is meant that any substituent on the compound may be substituted with $^{18}$F, $^{123}$I, $^{76}$Br, $^{124}$I and $^{75}$Br. For example, at least one of $R^{12}$ to $R^{36}$ in formula (III) or (IV) may be substituted with $^{18}$F, $^{123}$I, $^{76}$Br, $^{124}$I or $^{75}$Br. Typically one of $R^{12}$ to $R^{36}$ is substituted with $^{18}$F, $^{123}$I, $^{76}$Br, $^{124}$I and $^{75}$Br.

Typically, when the compound of formula (III) or (IV) is radiolabelled with $^{18}$F, $^{76}$Br, $^{124}$I and or $^{75}$Br, the image is obtained by positron emission tomography (PET) imaging. Typically, when the compound of formula (III) or (IV) is radiolabelled with $^{123}$I, the image is obtained by single positron emission computer tomography (SPECT) imaging.

A number of classes of TSPO ligands have been described in the literature. A compound which is effective as a therapeutic drug is not necessarily a compound that can be radiolabelled and used for imaging. Indeed, many drugs that are used therapeutically are not selective for a specific target and may interact with several targets to produce a therapeutic effect. Further, many therapeutic drugs do not have affinity that is in the nM range normally used for imaging, but have affinity in the μM range. In addition, the metabolism and lipophilicity of a therapeutic drug, particularly when administered at tracer levels for imaging, may make the drug unsuitable for use for imaging.

The present inventors have surprisingly found that compounds of formula (III) or (IV) radiolabelled with a radioisotope selected from $^{18}$F, $^{123}$I, $^{76}$Br, $^{124}$I and $^{75}$Br may be used to image TSPO and therefore microglial activation in a subject. The compounds of formula (III) or (IV) radiolabelled with $^{18}$F, $^{123}$I, $^{76}$Br, $^{124}$I or $^{75}$Br are selective ligands for TSPO and have high affinity for TSPO.

The compounds of (III) and (IV) radiolabelled with a radioisotope selected from $^{18}$F, $^{123}$I, $^{76}$Br, $^{124}$I and $^{75}$Br form salts, and salts of such compounds are encompassed by the present invention. The salts are preferably pharmaceutically acceptable, but it will be appreciated that non-pharmaceutically acceptable salts also fall within the scope of the present invention. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

A compound of formula (III) or (IV) can be radiolabelled with $^{18}$F, $^{123}$I, $^{76}$Br, $^{124}$I or $^{75}$Br by standard techniques known in organic chemistry for modifying an organic compound to replace a hydrogen or halo group in the compound with $^{18}$F, $^{123}$I, $^{76}$Br, $^{124}$I or $^{75}$Br.

Alternatively, compounds of formula (III) or (IV) radiolabelled with a radioisotope selected from $^{18}$F, $^{123}$I, $^{76}$Br, $^{124}$I and $^{75}$Br may be prepared by incorporating $^{18}$F, $^{123}$I, $^{76}$Br, $^{124}$I or $^{75}$Br as a substituent in one of the starting materials or in an intermediate used in the synthesis of compounds of formula (III) or (IV), for example, intermediate compounds of formula (V).

A compound of formula (III) or (IV) radiolabelled with $^{18}$F, $^{123}$I, $^{76}$Br, $^{124}$I or $^{75}$Br may, for example, be prepared by preparing a compound having the formula (III) or (IV) defined above, but in which one of $R^{12}$ to $R^{36}$ is substituted with a leaving group, such as tosylate, mesylate, Br or I, that allows an aliphatic nucleophilic substitution reaction to occur at the leaving group, and then subjecting the compound to conditions under which an aliphatic nucleophilic substitution reaction occurs to replace the leaving group with $^{18}$F, $^{123}$I, $^{76}$Br, $^{124}$I or $^{75}$Br. For example, when the leaving group is Br or tosylate, the compound may be reacted with the [$^{18}$F]-kryptofix-K222 complex in acetonitrile at about 80° C. for 10 minutes to form a compound of formula (III) or (IV) radiolabelled with $^{18}$F.

Compounds of formula (III) or (IV) radiolabelled with $^{123}$I, $^{76}$Br, $^{124}$I or $^{75}$Br may also be formed by forming a compound having the formula (III) or (IV) defined above, but in which one of $R^{12}$ to $R^{36}$ is substituted with a stannyl, silyl or halogen (the halogen substituent is usually different to the radioisotope), and subjecting the compound to an electrophilic substitution reaction in acetic media using an oxidising agent such as chloramine-T to form a compound of formula (III) or (IV) radiolabelled with $^{123}$I, $^{76}$Br, $^{124}$I or $^{75}$Br. In some embodiments, this reaction may be carried out at room temperature, and in other embodiments, the reaction mixture is heated to about 80° C. to 100° C. A compound of formula (III) or (IV) as defined above, but in which one of $R^{12}$ to $R^{36}$ is substituted with a leaving group may be modified by reactions known in organic chemistry to introduce a leaving group as a substituent on one of $R^{12}$ to $R^{36}$.

For example, in certain embodiments, compounds of formula (III) or (IV) may be radiolabelled on the phenyl substituent via an ethoxy group using a tosyl or fluoro precursor, or alternatively the acetamide functional group may be labelled directly by employing a tosyl or fluoro precursor.

The compounds of formula (III) or (IV) may be radiolabelled with $^{18}$F (half-life 110 minutes), $^{123}$I (half-life 13.2 hours), $^{76}$Br (half-life 16.2 hours), $^{124}$I (half-life 4.2 days) or $^{75}$Br (half-life 1.6 hours). Typically, the compounds of formula (III) or (IV) are radiolabelled with $^{18}$F. Compounds of formula (III) or (IV) radiolabelled with $^{18}$F, $^{123}$I, $^{76}$Br, $^{124}$I or $^{75}$Br are more practical in a clinical sense for imaging than compounds radiolabelled with radioisotopes having a significantly shorter half-life, as multiple scans can be performed on one day. In addition, hospitals/organisations that do not have a cyclotron on site can use such radioligands, as the radioligands can be prepared offsite and transported to the hospital/organisation with no significant loss of activity during transportation. In addition, longer scans (e.g. 180 minutes) can be undertaken with compounds labelled with $^{18}$F, $^{123}$I, $^{76}$Br, $^{124}$I or $^{75}$Br making them more appropriate for the study of most biological processes.

Compounds of formula (III) or (IV) radiolabelled with $^{18}$F, $^{123}$I, $^{76}$Br, $^{124}$I or $^{75}$Br have high affinity and selectivity for TSPO, and may be used for imaging TSPO in a subject. Accordingly, compounds of formula (III) or (IV) radiolabelled with $^{18}$F, $^{123}$I, $^{76}$Br, $^{124}$I or $^{75}$Br may be used to study TSPO in a subject.

In a subject having a neurodegenerative disorder, TSPO expression in the brain parenchyma is dramatically increased compared to a subject not having a neurodegenerative disorder. Accordingly, the compounds of formula (III) and (IV) radiolabelled with $^{18}$F, $^{123}$I, $^{76}$Br, $^{124}$I or $^{75}$Br may be used to study neurodegenerative disorders and may be used to diagnose and monitor the progression of neurodegenerative disorders. Neurodegenerative disorders that can be studied, diagnosed or monitored using these compounds include but are not limited to Alzheimer's disease, multiple sclerosis, Parkinson's disease, Huntington's disease, multiple system atrophy, epilepsy, encephalopathy, stroke and brain tumours. Each of these disorders is associated with neuronal injury or infection. Other disorders that may be studied, diagnosed or monitored using these compounds include but are not limited to glioblastoma, ischemic stroke, herpes encephalitis, HIV, amyotrophic lateral sclerosis, corticobasal degeneration, cancer, depression, auto-immune, infectious and neurodegenerative diseases.

In accordance with the present invention, a compound of formula (III) or (IV) radiolabelled with a radioisotope selected from $^{18}$F, $^{123}$I, $^{76}$Br, $^{124}$I and $^{75}$Br or a pharmaceutically acceptable salt thereof is administered to the subject.

When the compound of formula (III) or (IV) is radiolabelled with $^{18}$F, $^{76}$Br, $^{124}$I or $^{75}$Br, the image of the location of the radioisotope in the subject, and therefore the location of TSPO in the subject, may be obtained by positron emission tomography (PET) imaging using conventional techniques known the art. When the compound is radiolabelled with $^{123}$I, the image of the location of the radioisotope in the subject may be obtained by SPECT imaging using conventional techniques known in the art. Typically for both PET and SPECT imaging, the data is acquired using conventional dynamic or list mode acquisition techniques, commencing immediately after administration of the compound of formula (III) or (IV) radiolabelled with $^{18}$F, $^{123}$I, $^{76}$Br, $^{124}$I or $^{75}$Br or pharmaceutically acceptable salt thereof, and continuing for about 40 minutes or longer. At the completion of data acquisition, the data is typically processed to provide a time-series of 3D reconstructions, each depicting the distribution of the radioisotope in the body at a particular point in time.

Typically, the compound of formula (III) or (IV) radiolabelled with $^{18}$F, $^{123}$I, $^{76}$Br, $^{124}$I or $^{75}$Br or pharmaceutically acceptable salt thereof is administered parenterally. Typically, the compound of formula (III) or (IV) radiolabelled with $^{18}$F, $^{123}$I, $^{76}$Br, $^{124}$I or $^{75}$Br or pharmaceutically acceptable salt thereof is administered parenterally by intravenous injection or infusion. Typically the compound of formula (III) or (IV) radiolabelled with $^{18}$F, $^{76}$Br, $^{124}$I or $^{75}$Br or pharmaceutically acceptable salt thereof is administered at a dose in the range of about 5 to 20 mCi (185-740 MBq).

Typically, the compound of formula (III) or (IV) radiolabelled with $^{18}$F, $^{123}$I, $^{76}$Br, $^{124}$I or $^{75}$Br or pharmaceutically acceptable salt thereof is administered by administering a pharmaceutical composition comprising the compound of formula (III) or (IV) radiolabelled with $^{18}$F, $^{123}$I, $^{76}$Br, $^{124}$I or $^{75}$Br, or pharmaceutically acceptable salt thereof, and a pharmaceutically acceptable carrier.

Preparations for parenteral administration are typically in the form of a sterile aqueous or non-aqueous solution, suspension or emulsion. Examples of suitable non-aqueous solvents are propylene glycol, polyethylene glycol, vegetable oils such as olive oil, and injectable organic esters such as ethyl oleate. Suitable aqueous carriers include water and alcoholic/aqueous solutions, emulsions or suspensions, including saline and buffered media. Suitable parenteral vehicles include sodium chloride solution.

The salts of the compounds of formula (III) or (IV) are preferably pharmaceutically acceptable, but it will be appreciated that non-pharmaceutically acceptable salts also fall within the scope of the present invention. Non-pharmaceutically acceptable salts of the compounds of formula (III) or (IV) may be used as intermediates in the preparation of pharmaceutically acceptable salts of the compounds of formula (III) or (IV). Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

The compounds of formula (III) or (IV) are selective for TSPO and may activate TSPO. The activation of TSPO is related to increased synthesis of neurosteroids. The activation of TSPO can therefore increase the concentration of neurosteroids in the brain. These neurosteroids, including progesterone and dehydroepiandrosterone and their metabolites, positively modulate γ-aminobutyric acid (GABA) neurotransmission leading to nonsedative anxiolytic effects which are of therapeutic benefit in memory and stress related disorders. The compounds of formula (III) or (IV) may also be used as neuroprotective agents for the treatment of neurodegenerative disorders, as anti-inflammatory agents, and as anxiolytic agents.

Accordingly, in another aspect, the present invention provides a method of treating neurodegenerative disorders, inflammation or anxiety in a subject, comprising administering to the subject a therapeutically effective amount of a compound of formula (III) or (IV) or a pharmaceutically acceptable salt thereof. The neurodegenerative disorders that may be treated by the method include Alzheimer's disease, multiple sclerosis, Parkinson's disease, Huntington's disease, multiple system atrophy, epilepsy, encephalopathy, stroke and brain tumours. The compound of formula (III) or (IV) or pharmaceutically acceptable salt thereof is typically administered by administering a pharmaceutical composition comprising the compound of formula (III) or (IV) or pharmaceutically acceptable salt thereof.

In another aspect, the present invention provides a pharmaceutical composition comprising a compound of formula (III) or (IV) or a pharmaceutically acceptable salt thereof and a pharmaceutically acceptable carrier.

The composition of present invention comprises at least one compound of formula (III) or (IV) or a pharmaceutically acceptable salt thereof together with one or more pharmaceutically acceptable carriers and, optionally, other therapeutic agents. Suitable compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the compound of formula (III) or (IV) or pharmaceutically acceptable salt thereof with liquid carriers, diluents, adjuvants and/or excipients or finely divided solid carriers or both, and then, if necessary, shaping the product.

The term "subject" as used herein refers to any animal. The subject may be a mammal, e.g. a human. In some embodiments, the subject is a companion animal such as a dog or cat, a domestic animal such as a horse, pony, donkey, mule, llama, alpaca, pig, cow or sheep, or a zoo animal such as a primate, felid, canid, bovid or ungulate.

As used herein, the term "therapeutically effective amount" refers to an amount of a compound effective to yield a desired therapeutic response. The specific "therapeutically effective amount" will vary with such factors as the particular condition being treated, the physical condition of the subject, the type of subject being treated, the duration of the treatment, the nature of concurrent therapy (if any), and the specific formulation employed, and the attending clinician will be able to determine an appropriate therapeutically effective amount. For example, the attending clinician may determine an appropriate therapeutically effective amount of a compound of formula (III) or (IV) or a pharmaceutically acceptable salt thereof having regard to conventional dosages of other neurologically active compounds or the results of animal experiments. In some embodiments, the compound of formula (III) or (IV) or pharmaceutically acceptable salt thereof may be administered at a dosage of about 1 to about 20 mg/kg bodyweight/day.

As used herein, a "pharmaceutically acceptable carrier" is a pharmaceutically acceptable solvent, suspending agent or vehicle for delivering a compound to a subject. The carrier may be in any form including a solid, liquid or gas and is selected with the planned manner of administration in mind. The carrier is "pharmaceutically acceptable" in the sense of being not biologically or otherwise undesirable, i.e. the carrier may be administered to a subject along with the active ingredient without causing any or a substantial adverse reaction.

The compounds of formula (III) or (IV) or pharmaceutically acceptable salt thereof may be administered orally, topically or parenterally (e.g. by subcutaneous injection, by aerosol administration to the lungs or nasal cavity, or by intravenous, intramuscular, intrathecal or intracranial injection or infusion techniques) in a dosage unit formulation containing conventional non-toxic pharmaceutically acceptable carriers.

The compounds of formula (III) or (IV) or pharmaceutically acceptable salt thereof may be administered orally as tablets, aqueous or oily suspensions, lozenges, troches, powders, granules, emulsions, capsules, syrups or elixirs. A composition for oral use may contain one or more agents selected from the group of sweetening agents, flavouring agents, colouring agents, disintegrating agents, lubricants, time delay agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Preparations for parenteral administration are typically in the form of a sterile aqueous or non-aqueous solution, suspension or emulsion. Examples of suitable non-aqueous solvents are propylene glycol, polyethylene glycol, vegetable oils such as olive oil, and injectable organic esters such as ethyl oleate. Suitable aqueous carriers include water and alcoholic/aqueous solutions, emulsions or suspensions, including saline and buffered media. Suitable parenteral vehicles include sodium chloride solution. Preservatives and other additives may also be present such as, for example, antimicrobials, anti-oxidants, chelating agents, growth factors, inert gases, and the like.

Generally, the terms "treating", "treatment" and the like are used herein to mean affecting a subject to obtain a desired pharmacological and/or physiological effect. The effect may be prophylactic in terms of completely or partially preventing a disease or disorder or sign or symptom thereof, and/or may be therapeutic in terms of a partial or complete cure of a disease or disorder. "Treating" as used herein covers any treatment of, or prevention of, disease or disorder in a vertebrate, a mammal, particularly a human, and includes: (a) preventing the disease or disorder from occurring in a subject that may be predisposed to the disease or disorder, but has not yet been diagnosed as having the disease or disorder; (b) inhibiting the disease or disorder, i.e., arresting the development of the disease or disorder; or (c) relieving or ameliorating the effects of the disease or disorder, i.e. causing regression of the effects of the disease or disorder.

EXAMPLES

Embodiments of the invention are described below by reference to the following non-limited examples.

Preparation of 6,8-dimethyl-[1,2,4]triazolo[4,3-b]pyridazine (1)

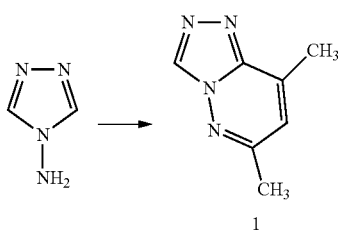

Method A 2,4-Pentanedione (1.9 g, 11.9 mmol) was added to a solution of 4-amino-1,2,4-triazole (1.00 g, 11.9 mmol) in EtOH (30 mL) and heated at reflux for 14 h. The reaction mixture was allowed to cool and the solvent was then evaporated to dryness. The residue was purified by silica gel column chromatography (dichloromethane/MeOH, 20:1 v/v as eluent) which yielded 1 (0.46 g, 26%) as pale yellow crystals; mp: 106-109° C.; $^1$H NMR (CDCl$_3$, 300 MHz) δ: 2.54 (s, 3H), 2.70 (s, 3H), 6.81 (s, 1H), 8.98 (s, 1H).

Method B 2,4-Pentanedione (6.0 g, 60 mmol) and p-toluene sulfonic acid (0.06 g, 0.35 mmol) were added to a solution of 4-amino-1,2,4-triazole (5 g, 60 mmol) in anhydrous toluene (25 mL) and heated at reflux for 7 h using a Dean Stark trap. Once the reaction was complete, the resulting yellow, transparent solution was allowed to cool to room temperature and evaporated to dryness. The crude oil was dissolved in CHCl$_3$ and washed with saturated NaHCO$_3$ aqueous solution. The organic layer was isolated, dried over anhydrous Na$_2$SO$_4$ and evaporated to dryness, yielding the pure product 1 (7.65 g, 87%) as light yellow crystals. $^1$H NMR (CDCl$_3$, 300 MHz) δ: 2.54 (s, 3H), 2.70 (s, 3H), 6.81 (s, 1H), 8.98 (s, 1H).

Preparation of 6,8-dimethyl-2-(2-oxo-2-phenylethyl)-[1,2,4]triazolo[4,3-b]pyridazin-2-ium (2)

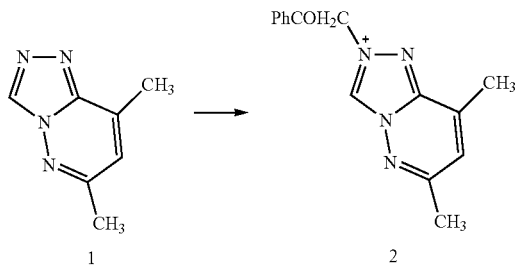

Bromoacetophenone (2.70 g, 13.5 mmol) was added to a solution of 1 (2.00 g, 13.5 mmol) in nitromethane (35 mL) and heated at reflux under an inert atmosphere for 2.5 h. The reaction mixture was allowed to cool and the solvent was evaporated to dryness to afford a red, sticky oil. The crude oil was purified by silica gel column chromatography (CHCl$_3$/MeOH, 7:1 (v/v), as eluent), which afforded 2 (2.7 g, 75%) as orange crystals; mp: 189-192° C. $^1$H NMR (CDCl$_3$, 300 MHz) δ: 2.70 (s, 6H), 6.98 (s, 2H), 7.28 (d, J=1.5 Hz, 1H), 7.55 (t, J=7.5 Hz, 2H), 7.69 (tt, J=1.2, 7.4 Hz, 1H), 8.08 (d, J=1.2 Hz, 2H), 11.89 (s, 1H). Mass Spectrum: CI, m/z 268 (M+1).

Preparation of 4,6-dimethylpyridazin-3-amine (3)

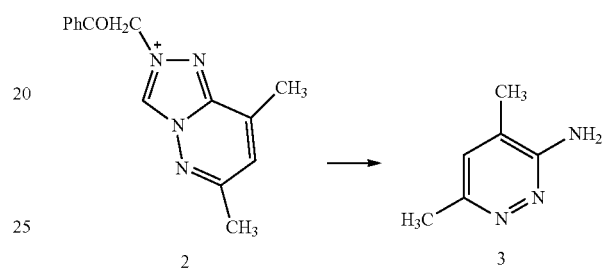

A solution of alkylated salt 2 (2.58 g, 9.65 mmol) in 20% aqueous NaOH solution (29.0 mmol) was heated at reflux for 16 h. The crude reaction mixture was evaporated to dryness and purified by silica gel column chromatography (CHCl$_3$/MeOH, 10:1 (v/v), as eluent), to yield 3 (1.1 g, 93%) as a pale, brown powder; mp: 123-126° C. $^1$H NMR (CDCl$_3$, 300 MHz) δ: 2.13 (s, 3H), 2.50 (s, 3H), 6.93 (s, 1H). Mass Spectrum: CI, m/z 124 (M+1).

General Procedure for Synthesis of Compounds 4a-e

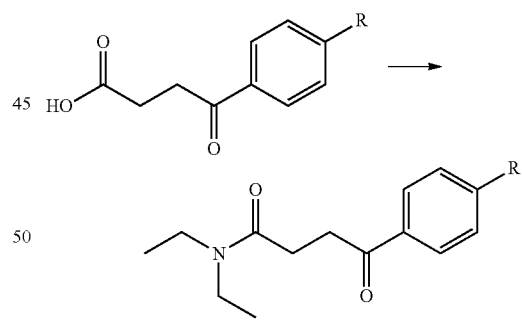

R =
(a) OCH$_3$,
(b) CH$_3$,
(c) Cl,
(d) Br,
(e) F

A solution of the appropriate oxobutanoic acid (24 mmol), diethylamine (2.70 mL, 26.4 mmol), triethylamine (13 mL, 36 mmol) and EEDQ (7.20 g, 28.8 mmol) in anhydrous THF (100 mL) was heated at reflux overnight. The reaction mixture was allowed to cool and the solvent was removed in vacuo. The remaining residue was acidified with dilute HCl (10%) and then neutralised with dilute NaOH (5%). The neutral solution was washed with water and extracted with CHCl₃. The organic layer was dried over Na₂SO₄ and evaporated to yield a dark, red oil. The oil was cooled to 0° C. Ethyl acetate (30 mL) was added to the cooled oil and the resulting crystals were filtered and washed with petroleum ether to yield the corresponding amide product.

Preparation of
N,N-diethyl-4-(4-methoxyphenyl)-4-oxobutanamide
(4a)

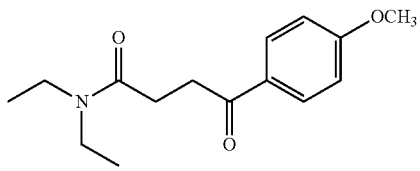 [SMILES: CCN(CC)C(=O)CCC(=O)c1ccc(OC)cc1]

This compound was obtained from 4-(4-methoxyphenyl)-4-oxobutanoic acid (5.0 g, 24 mmol) as light yellow crystals; 5.2 g, 83%; mp: 59-62° C. ¹H NMR (CDCl₃, 300 MHz) δ: 1.09-1.26 (m, 6H), 2.76 (t, J=6.9 Hz, 2H), 3.30-3.41 (m, 6H), 3.87 (s, 3H), 6.93 (d, J=9.0 Hz, 2H), 8.00 (d, J=9.0 Hz, 2H).

Preparation of
N,N-diethyl-4-oxo-4-p-tolylbutanamide (4b)

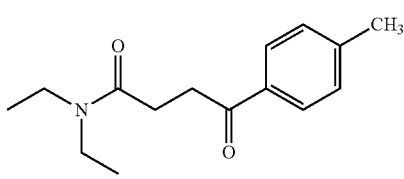 [SMILES: CCN(CC)C(=O)CCC(=O)c1ccc(C)cc1]

This compound was obtained from 4-oxo-4-p-tolylbutanoic acid (4.6 g, 24 mmol) as light yellow crystals; 4.7 g, 80%; mp: 63-66° C. ¹H NMR (CDCl₃, 300 MHz) δ: 1.08-1.26 (m, 6H), 2.41 (s, 3H), 2.76 (t, J=6.9 Hz, 2H), 3.30-3.42 (m, 6H), 7.25 (d, J=8.4 Hz, 2H), 7.93 (d, J=8.4 Hz, 2H).

Preparation of
4-(4-chlorophenyl)-N,N-diethyl-4-oxobutanamide
(4c)

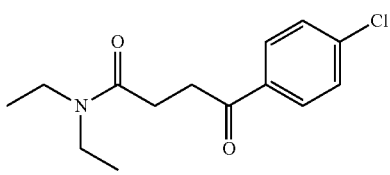 [SMILES: CCN(CC)C(=O)CCC(=O)c1ccc(Cl)cc1]

This compound was obtained from 4-(4-chlorophenyl)-4-oxobutanoic acid (5.1 g, 24 mmol) as pale, brown crystals; 5.3 g, 83%; mp: 85-88° C. ¹H NMR (CDCl₃, 300 MHz) δ: 1.08-1.26 (m, 6H), 2.77 (t, J=6.6 Hz, 2H), 3.30-3.43 (m, 6H), 7.43 (d, J=6.9 Hz, 2H), 7.96 (d, J=6.9 Hz, 2H).

Preparation of
4-(4-bromophenyl)-N,N-diethyl-4-oxobutanamide
(4d)

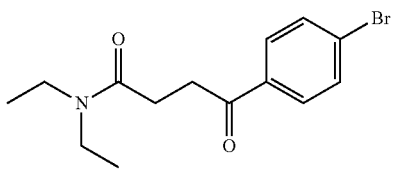 [SMILES: CCN(CC)C(=O)CCC(=O)c1ccc(Br)cc1]

This compound was obtained from 4-(4-bromophenyl)-4-oxobutanoic acid (6.2 g, 24 mmol) as lustrous, white crystals; 6.0 g, 80%; mp: 90-93° C. ¹H NMR (CDCl₃, 300 MHz) δ: 1.08-1.26 (m, 6H), 2.77 (t, J=6.6 Hz, 2H), 3.29-3.43 (m, 6H), 7.59 (d, J=6.6 Hz, 2H), 7.89 (d, J=6.6 Hz, 2H).

Preparation of
N,N-diethyl-4-(4-fluorophenyl)-4-oxobutanamide
(4e)

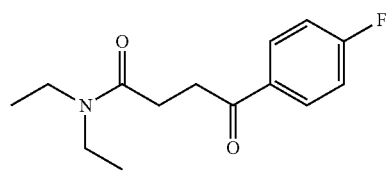 [SMILES: CCN(CC)C(=O)CCC(=O)c1ccc(F)cc1]

This compound was obtained from 4-(4-fluorophenyl)-4-oxobutanoic acid (4.7 g, 24 mmol) as tangerine crystals; 5.1 g, 85%; mp: 48-51° C. ¹H NMR (CDCl₃, 300 MHz) δ: 1.08-1.26 (m, 6H), 2.78 (t, J=6.6 Hz, 2H), 3.30-3.44 (m, 6H), 7.09-7.15 (m, 2H), 8.02-8.07 (m, 2H).

General Procedure for Synthesis of Compounds 5a-e

Bromine (0.4 mL, 7.6 mmol) was slowly added to a solution of the suitable amide 4a-e (7.6 mmol) in CHCl₃ (~20 mL) at 0° C. and stirred for 1 h. The reaction was then stirred at room temperature overnight. The reaction mixture was evaporated to dryness and the residue was purified by silica gel column chromatography (petroleum ether/ethyl acetate, 50:50 (v/v), as eluent), to yield the respective brominated product.

Scheme 5.
(i) TEA, Diethylamine, THF, EEDQ, reflux 12 h; (ii) Br$_2$, CHCl$_3$, 0° C. 1 h, RT overnight; (iii) DMF, reflux 24 h

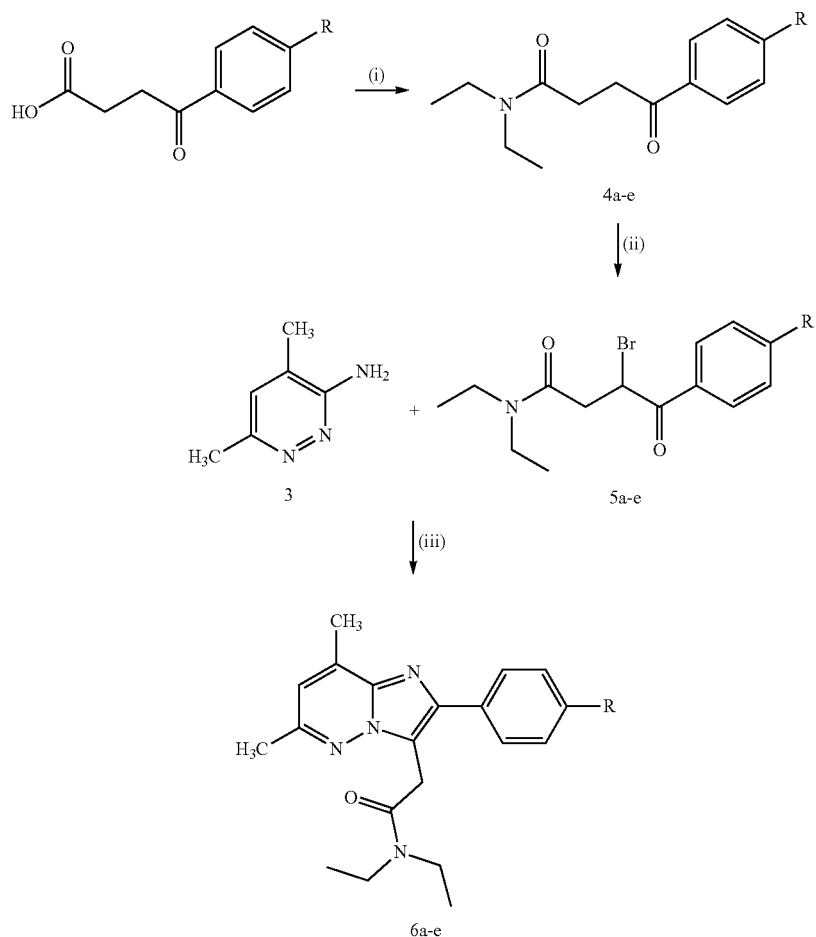

R =
(a) OCH$_3$,
(b) CH$_3$,
(c) Cl,
(d) Br,
(e) F

Preparation of 3-bromo-N,N-diethyl-4-(4-methoxyphenyl)-4-oxobutanamide (5a)

Preparation of 3-bromo-N,N-diethyl-4-oxo-4-p-tolylbutanamide (5b)

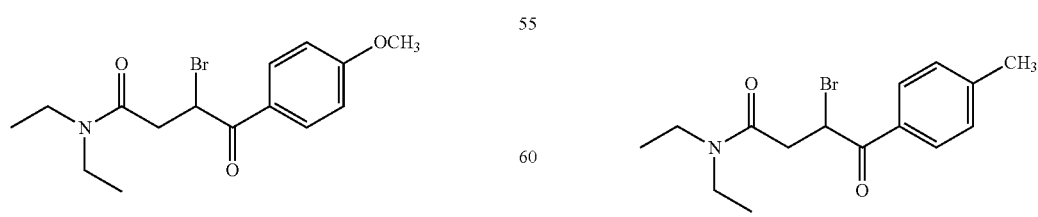

Pale yellow oil obtained from 4a (2 g, 7.6 mmol); 2.47 g, 95%. $^1$H NMR (CDCl$_3$, 300 MHz) δ: 1.05-1.29 (m, 6H), 3.00-3.58 (m, 6H), 3.87 (s, 3H), 5.62-5.78 (m, 1H), 6.95 (d, J=9.0 Hz, 2H), 8.04 (d, J=9.0 Hz, 2H).

Yellow oil obtained from 4b (1.88 g, 7.6 mmol); 1.9 g, 78%. $^1$H NMR (CDCl$_3$, 300 MHz) δ: 1.04-1.29 (m, 6H), 2.41 (s, 3H), 3.01-3.59 (m, 6H), 5.65-5.79 (m, 1H), 7.27 (d, J=8.4 Hz, 2H), 7.96 (d, J=8.4 Hz, 2H).

Preparation of 3-bromo-4-(4-chlorophenyl)-N,N-diethyl-4-oxobutanamide (5c)

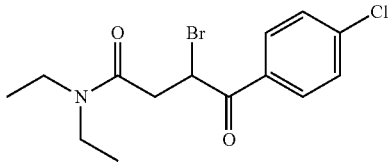 [SMILES: CCN(CC)C(=O)CC(Br)C(=O)c1ccc(Cl)cc1]

Fluorescent green oil obtained from 4c (2.0 g, 7.6 mmol); 2.36 g, 90%. $^1$H NMR (CDCl$_3$, 300 MHz) δ: 1.04-1.29 (m, 6H), 3.01-3.62 (m, 6H), 5.59-5.67 (m, 1H), 7.46 (d, J=8.7 Hz, 2H), 7.99 (d, J=8.7 Hz, 2H).

Preparation of 3-bromo-4-(4-bromophenyl)-N,N-diethyl-4-oxobutanamide (5d)

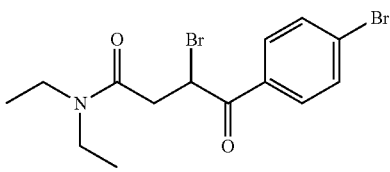 [SMILES: CCN(CC)C(=O)CC(Br)C(=O)c1ccc(Br)cc1]

Pale yellow oil obtained from 4d (3.75 g, 12 mmol); 4.12 g, 88%. $^1$H NMR (CDCl$_3$, 300 MHz) δ: 1.04-1.28 (m, 6H), 3.01-3.61 (m, 6H), 5.56-5.61 (m, 1H), 7.60-7.64 (m, 2H), 7.89-7.94 (m, 2H).

Preparation of 3-bromo-N,N-diethyl-4-(4-fluorophenyl)-4-oxobutanamide (5e)

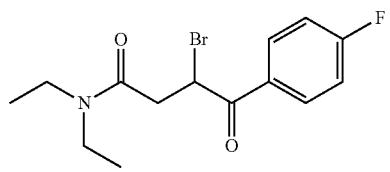 [SMILES: CCN(CC)C(=O)CC(Br)C(=O)c1ccc(F)cc1]

Pale yellow oil obtained from 4e (1.58 g, 6.2 mmol); 1.72 g, 84%. $^1$H NMR (CDCl$_3$, 300 MHz) δ: 1.04-1.29 (m, 6H), 3.01-3.62 (m, 6H), 5.92-5.64 (m, 1H), 7.12-7.26 (m, 2H), 8.06-8.12 (m, 2H).

General Procedure for Synthesis of Compounds 6a-e

A solution of brominated amide 5a-e (6.18 mmol) in anhydrous DMF (10 mL) was added to a mixture of 3 (6.18 mmol) in anhydrous DMF (10 mL) and heated at reflux for 24 h under an inert atmosphere. The crude reaction mixture was allowed to cool, evaporated to dryness and purified via silica gel column chromatography using ethyl acetate as an eluent, to yield the corresponding dimethylimidazopyridazine.

Preparation of N,N-diethyl-2-(2-(4-methoxyphenyl)-6,8-dimethylimidazo[1,2-b]pyridazin-3-yl)ethanamide (6a)

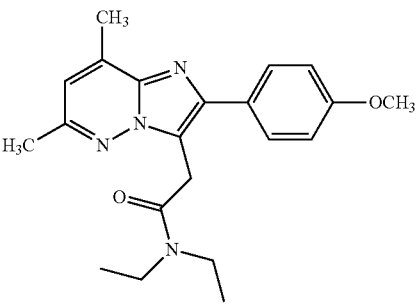 [SMILES: CCN(CC)C(=O)Cc1c(-c2ccc(OC)cc2)nc2c(C)cc(C)nn12]

Light brown crystals obtained from 5a (2.1 g, 6.18 mmol); 1.2 g, 54%, mp: 129-131° C. $^1$H NMR (CDCl$_3$, 300 MHz) δ: 1.16-1.32 (m, 6H), 2.50 (s, 3H), 2.65 (s, 3H), 3.42-3.58 (m, 4H), 3.84 (s, 3H), 4.11 (s, 2H), 6.71 (s, 1H), 6.98 (d, J=8.7 Hz, 2H), 7.79 (d, J=8.7 Hz, 2H); Found: C, 65.05; H, 6.30; N, 14.18. Mass Spectrum: CI, m/z 367 (M+1).

Preparation of 2-(6,8-dimethyl-2-p-tolylimidazo[1,2-b]pyridazin-3-yl)-N,N-diethylethanamide (6b)

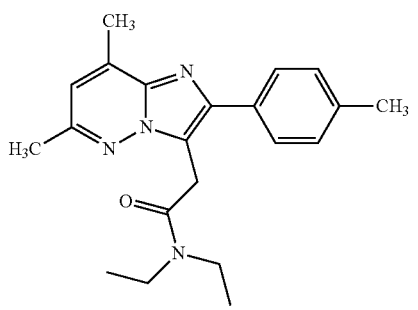

Light brown crystals obtained from 5b (1.0 g, 2.9 mmol); 0.50 g, 50%, mp: 155-158° C. $^1$H NMR (CDCl$_3$, 300 MHz) δ: 1.13-1.32 (m, 6H), 2.39 (s, 3H), 2.43 (s, 3H), 2.64 (s, 3H), 3.44-3.55 (m, 4H), 4.12 (s, 2H), 6.70 (s, 1H), 7.25 (d, J=8.2 Hz, 2H), 7.72 (d, J=8.2 Hz, 2H); Found: C, 63.58; H, 6.92; N, 13.92. Mass Spectrum: CI, m/z 351 (M+1).

Preparation of 2-(2-(4-chlorophenyl)-6,8-dimethylimidazo[1,2-b]pyridazin-3-yl)-N,N-diethylethanamide (6c)

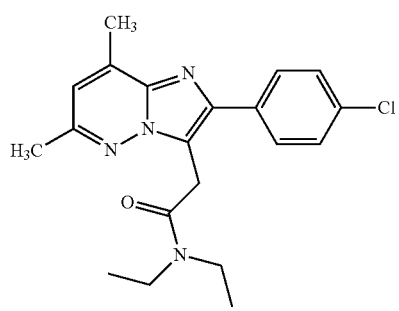 [SMILES: CCN(CC)C(=O)Cc1c(-c2ccc(Br)cc2)nc2c(C)cc(C)nn12]

Light brown crystals obtained from 5c (0.95 g, 2.9 mmol); 0.57 g, 53%, mp: 162-165° C. $^1$H NMR (CDCl$_3$, 300 MHz) δ:

1.13-1.34 (m, 6H), 2.50 (s, 3H), 2.64 (s, 3H), 3.44-3.57 (m, 4H), 4.11 (s, 2H), 6.73 (s, 1H), 7.41 (d, J=8.7 Hz, 2H), 7.81 (d, J=8.7 Hz, 2H); Found: C, 63.46; H, 6.30; N, 14.49. Mass Spectrum: CI, m/z 371 (M+1).

Preparation of 2-(2-(4-bromophenyl)-6,8-dimethylimidazo[1,2-b]pyridazin-3-yl)-N,N-diethylacetamide (6d)

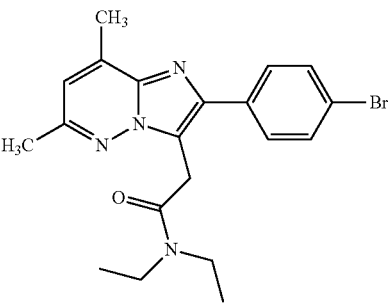

Light brown crystals obtained from 5d (1.00 g, 2.6 mmol); 0.55 g, 51%, mp: 171-175° C. ¹H NMR (CDCl₃, 300 MHz) δ: 1.13-1.34 (m, 6H), 2.50 (s, 3H), 2.64 (s, 3H), 3.42-3.60 (m, 4H), 4.10 (s, 2H), 6.72 (s, 1H), 7.56 (d, J=8.7 Hz, 2H), 7.75 (d, J=8.7 Hz, 2H); Found: C, 57.47; H, 5.50; N, 12.87. Mass Spectrum: CI, m/z 415 (M+1).

Preparation of N,N-diethyl-2-(2-(4-fluorophenyl)-6,8-dimethylimidazo[1,2-b]pyridazin-3-yl)acetamide (6e)

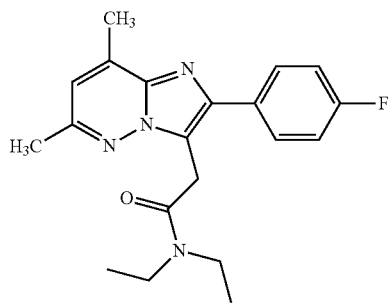 [SMILES: CCN(CC)C(=O)Cc1c(-c2ccc(F)cc2)nc2c(C)cc(C)nn12]

Light brown crystals obtained from 5e (0.67 g, 1.7 mmol); 0.33 g, 55%, mp: 139-143° C. ¹H NMR (CDCl₃, 300 MHz) δ: 1.13-1.34 (m, 6H), 2.50 (s, 3H), 2.64 (s, 3H), 3.42-3.60 (m, 4H), 4.10 (s, 2H), 6.71 (s, 1H), 7.10-7.16 (m, 2H), 7.82-7.87 (m, 2H); Found: C, 67.29; H, 6.60; N, 14.99. Mass Spectrum: CI, m/z 355 (M+1).

Preparation of N,N-diethyl-2-(2-(4-hydroxyphenyl)-6,8-dimethylimidazo[1,2-b]pyridazin-3-yl)ethanamide (7)

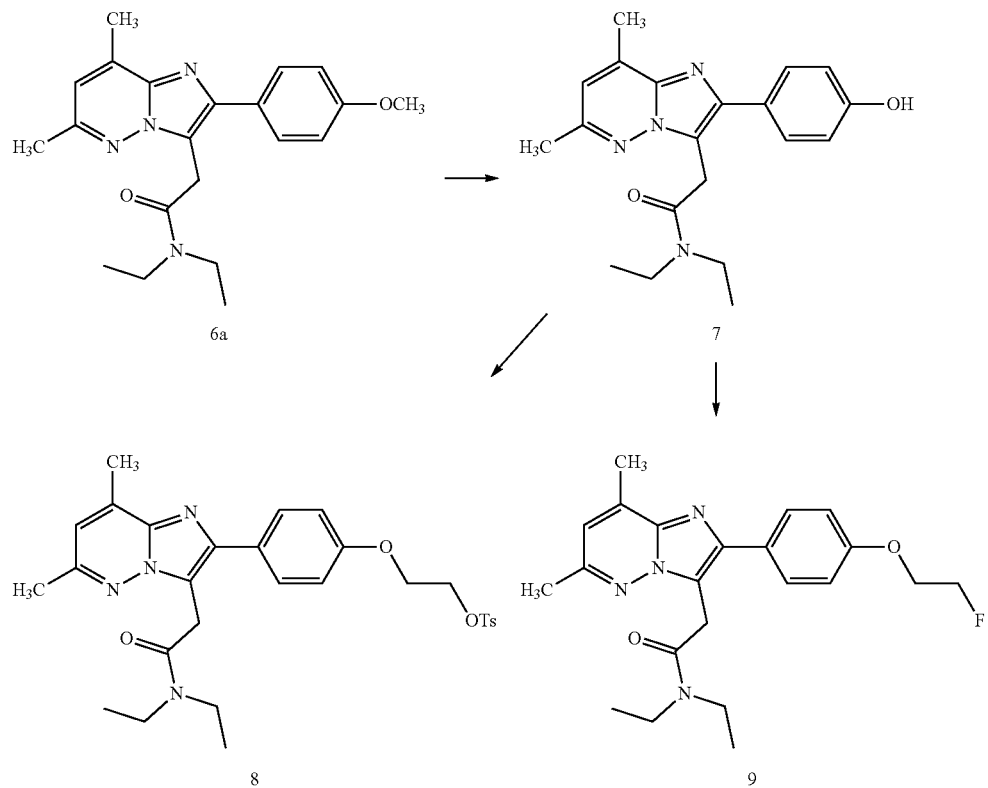

Scheme 6.

Method A

BBr$_3$ (2.87 mL, 2.87 mmol) was added dropwise to a solution of methoxy pyridazine 6a (0.7 g, 1.9 mmol) in anhydrous dichloromethane (40 mL) at 0° C. After stirring for 1 h at 0° C., a further 1.5 equiv. of BBr$_3$ (2.87 mL, 2.87 mmol) was added dropwise and the mixture was stirred at rt for 16 h. Following this, the reaction mixture was quenched with MeOH (~20 mL) and evaporated to dryness. The resulting brown solid was washed with CHCl$_3$ and purified via column chromatography (eluent; dichloromethane/MeOH, 10:1 v/v) to yield 7 (0.49 g, 1.4 mmol) as a tan coloured powder in 73% yield, mp: 266-268° C. $^1$H NMR (DMSO, 300 MHz) δ: 1.01-1.26 (m, 6H), 2.44 (s, 3H), 2.53 (s, 3H), 3.24-3.55 (m, 4H), 4.08 (s, 2H), 6.82 (d, J=8.7 Hz, 2H), 6.94 (s, 1H), 7.56 (d, J=8.4 Hz, 2H); Found: C, 63.40; H, 6.59; N, 13.59. Mass Spectrum: CI, m/z 353 (M+1).

Method B

A solution of the methoxy pyridazine 6a (0.25 g, 0.68 mmol), hexadecyl tributyl phosphonium bromide (0.023 g, 0.068 mmol) and 45% HBr (4.5 mL) was heated at 100° C. for 7 h under constant stirring. The reaction mixture was basified to pH 8-9 using NaHCO$_3$ and extracted with CH$_2$Cl$_2$. The organic layer was collected and dried over anhydrous Na$_2$SO$_4$. The solvent was removed under vacuum and the residue was purified by column chromatography to yield 7.

Preparation of 2-(4-(3-(2-(diethylamino)-2-oxoethyl)-6,8-dimethylimidazo[1,2b]pyridazin-2-yl)phenoxy)ethyl 4-methylbenzenesulfonate (8)

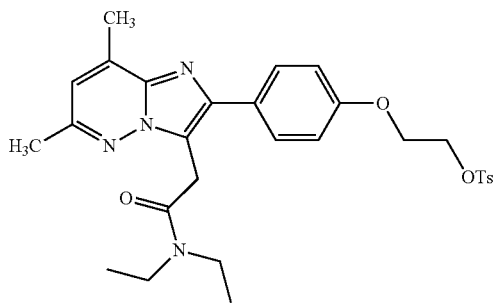

8

Method A

Diisopropyl azodicarboxylate (DIAD, 0.21 mL, 1.1 mmol) was added to a solution of 7 (176 mg, 0.5 mmol) triphenylphosphine (285 mg, 1.1 mmol) and toluene-4-sulfonic acid 2-hydroxy-ethyl ester (235 mg, 1.1 mmol) in anhydrous DMF (10 mL). The reaction mixture was stirred for 20 h at rt and then concentrated in vacuo (95° C., 20 mbar). The resulting crude oil was dissolved in CHCl$_3$ (40 mL) and washed with water (3×20 mL) to remove traces of DMF. The organic layer was isolated and dried over anhydrous Na$_2$SO$_4$. The solvent was removed in vacuo and the residue was purified by column chromatography (CHCl$_3$/MeOH, 80:1 v/v as eluent) to yield 8 (10 mg, 0.018 mmol) as pale yellow crystals in 4% yield. $^1$H NMR (CDCl$_3$, 300 MHz) δ: 1.13-1.28 (m, 6H), 2.45 (s, 3H), 2.49 (s, 3H), 2.63 (s, 3H), 3.42-3.58 (m, 4H), 4.10 (s, 2H), 4.16-4.20 (m, 2H), 4.37-4.40 (m, 2H), 6.70 (s, 1H), 6.85 (d, J=6.9 Hz, 2H), 7.34 (d, J=7.8 Hz, 2H), 7.76 (d, J=6.9 Hz, 2H), 7.84 (d, J=7.8 Hz, 2H).

Method B

A solution of 7 (0.175 g, 0.50 mmol) in anhydrous DMF (~7 mL) was added to sodium hydride (0.05 g, 60% dispersion in oil, 1.25 mmol) in anhydrous DMF (~7 mL). After stirring at 0° C. for 1 h, ethylene glycol di-p-tosylate (0.736 g, 2 mmol) was dissolved in anhydrous DMF (~2 mL) and slowly added to the main reaction solution. The mixture was then allowed to stir at room temperature for 12 h, after which the solution was concentrated in vacuo (95° C., 20 mbar). The resin thus obtained was extracted with dichloromethane and washed twice with a saturated aqueous solution of ammonium chloride. The organic layer was then washed with water four times (to remove any remaining DMF), dried over anhydrous magnesium sulfate and evaporated to dryness. The resulting crude oil was purified via column chromatography using ethyl acetate as an eluent to afford 8 (130 mg, 0.24 mmol) in 47% yield as yellow crystals; mp: 120-123° C.; $^1$H NMR (CDCl$_3$, 300 MHz) δ: 1.13-1.28 (m, 6H), 2.45 (s, 3H), 2.49 (s, 3H), 2.63 (s, 3H), 3.42-3.58 (m, 4H), 4.10 (s, 2H), 4.16-4.20 (m, 2H), 4.37-4.40 (m, 2H), 6.70 (s, 1H), 6.85 (d, J=6.9 Hz, 2H), 7.34 (d, J=7.8 Hz, 2H), 7.76 (d, J=6.9 Hz, 2H), 7.84 (d, J=7.8 Hz, 2H); Found: C, 63.06; H, 6.44; N, 10.12. Mass Spectrum: CI, m/z 551 (M+1).

Preparation of 2-fluoroethyl-4-methylbenzenesulfonate

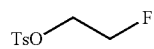

A solution of pyridine (17 mL, 0.21 moles), p-toluenesulfonyl chloride (3.57 g, 18.73 mmol) and fluoroethanol (1 mL, 17.03 mmol) was stirred at 0° C. for 1 h and at room temperature for a further 14 h under an argon atmosphere. The pale transparent mixture was quenched with ice-water (~30 mL) and shaken for 5 min to hydrolyse any unreacted tosyl chloride. The suspension was extracted with ethyl acetate (~15 mL) and the excess pyridine was neutralised by adding dilute sulphuric acid (containing crushed ice) to the organic layer. The organic layer was then washed with more dilute sulphuric acid (containing crushed ice), ice-water, dilute potassium hydroxide (containing crushed ice) and again with ice-water. Following this, the ether solution was dried over anhydrous sodium sulphate and the solvent was removed in vacuo to afford 2-fluoroethyl-4-methylbenzenesulfonate (1.40 g, 6.41 mmol) in 38% yield as a clear oil. $^1$H NMR (CDCl$_3$, 300 MHz) δ: 3.58 (s, 3H), 4.19-4.31 (m, 2H), 4.47-4.66 (m, 2H), 7.36 (d, J=8.4 Hz, 2H), 7.80 (d, J=8.4 Hz, 2H).

Preparation of N,N-diethyl-2-(2-(4-(2-fluoroethoxy) phenyl)-6,8-dimethylimidazo-[1,2-b]pyridazin-3-yl) ethanamide (9, PDAZ-FE)

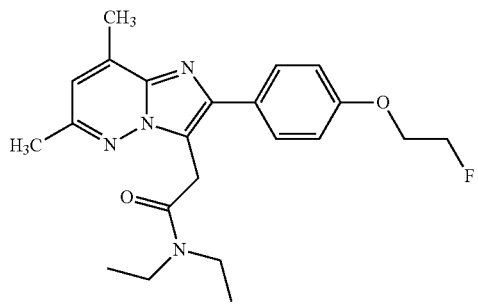

Method A

Diisopropyl azodicarboxylate (DIAD, 190 mg, 0.94 mmol) was added to a solution of 7 (150 mg, 0.43 mmol), triphenylphosphine (274 mg, 0.94 mmol) and 2-fluoroethanol (60 mg, 0.94 mmol) in anhydrous DMF (6 mL). The reaction mixture was stirred at room temperature for 48 h and then concentrated in vacuo (95° C., 20 mbar). The resulting crude oil was dissolved in CHCl$_3$ (40 mL) and washed with water (3×20 mL) to remove traces of DMF. The organic layer was isolated and dried over anhydrous Na$_2$SO$_4$. The solvent was removed in vacuo and the residue was purified by column chromatography (CHCl$_3$/MeOH, 80:1 v/v as eluent) to yield 9 (15 mg, 0.038 mmol) as pale yellow crystals in 9% yield. $^1$H NMR (CDCl$_3$, 300 MHz) δ: 1.13-1.32 (m, 6H), 2.49 (s, 3H), 2.64 (s, 3H), 3.42-3.58 (m, 4H), 4.11 (s, 2H), 4.26 (dt, J=4, 28 Hz, 2H), 4.78 (dt, J=4, 47 Hz, 2H), 6.70 (s, 1H), 7.01 (d, J=9.0 Hz, 2H), 7.79 (d, J=9.0 Hz, 2H).

Method B

A solution of 7 (0.20 g, 0.57 mmol) in anhydrous DMF (~7 mL) was added to sodium hydride (0.046 g, 60% dispersion in oil, 1.14 mmol) in anhydrous DMF (~7 mL). After stirring at 0° C. for 1 h, a solution of 2-fluoroethyl-4-methylbenzene-sulfonate (0.125 g, 0.57 mmol) in anhydrous DMF (~2 mL) was slowly added to the main reaction solution. The mixture was then allowed to stir at rt for 12 h, after which the solution was concentrated in vacuo (95° C., 20 mbar). The resin was extracted with dichloromethane and washed with a saturated solution of ammonium chloride twice. The organic layer was then washed with water four times (to remove any remaining DMF), dried over anhydrous magnesium sulfate and evaporated to dryness. The resulting crude oil was purified via column chromatography using ethyl acetate as an eluent to afford 9 (130 mg, 0.33 mmol) as yellow crystals in 58% yield; mp: 149-151° C.; $^1$H NMR (CDCl$_3$, 300 MHz) δ: 1.13-1.32 (m, 6H), 2.49 (s, 3H), 2.64 (s, 3H), 3.42-3.58 (m, 4H), 4.11 (s, 2H), 4.26 (dt, J=4, 28 Hz, 2H), 4.78 (dt, J=4, 47 Hz, 2H,), 6.70 (s, 1H), 7.01 (d, J=9.0 Hz, 2H), 7.79 (d, J=9.0 Hz, 2H); Found: C, 66.68; H, 7.03; N, 14.07. Mass Spectrum: CI, m/z 399 (M+1).

2. Synthesis of Carboxylic Acid Intermediates

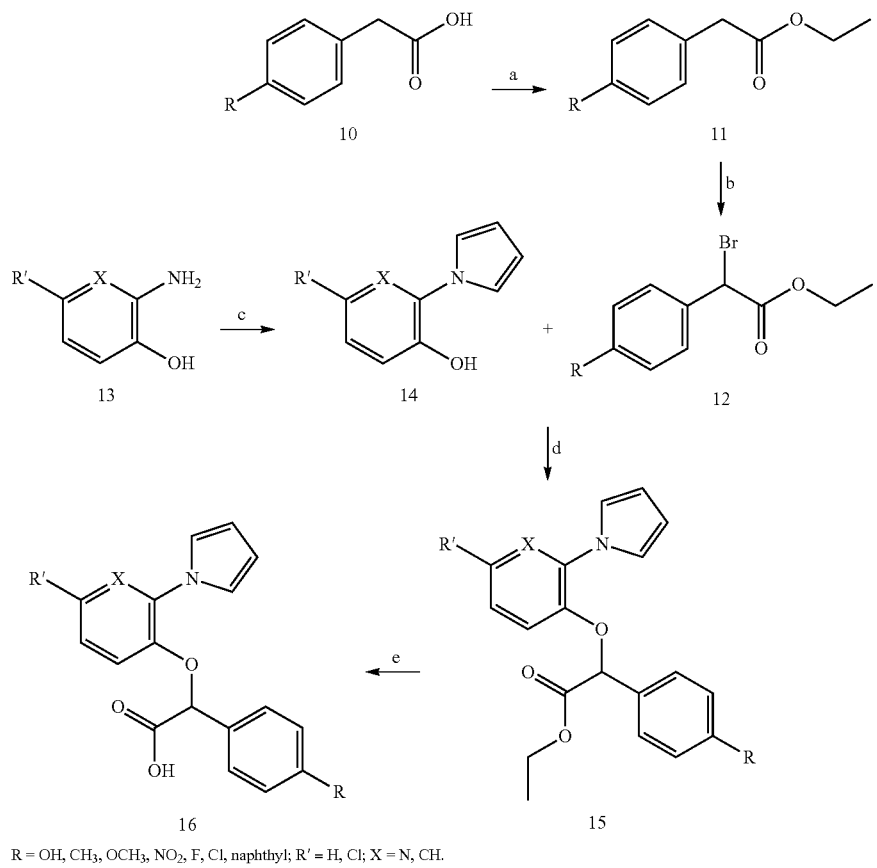

Scheme 7: Reagents: (a) EtOH, H$_2$SO$_4$ (b) N-bromosuccinimide, dibenzoyl peroxide (c) 2,5-dimethoxytetrahydrofuran, glacial acetic acid (d) NaH (e) 10% NaOH.

R = OH, CH$_3$, OCH$_3$, NO$_2$, F, Cl, naphthyl; R' = H, Cl; X = N, CH.

General Procedure for Synthesis of Compounds 10 to 16

The appropriate phenyl acetic acid 10 was dissolved in anhydrous ethanol and refluxed in the presence of a catalytic amount of sulfuric acid to produce the ethyl ester 11. The ethyl ester was then refluxed in chloroform for 24 h using an equimolar amount of freshly recrystallised N-bromosuccinimide and a catalytic quantity of benzoyl peroxide to produce the α-bromo-arylester 12. The pyrrole 14 was produced by refluxing of the appropriate aminophenol (or may be prepared from an aminopyridinol) 13 in glacial acetic acid for 4 h using a molar equivalent of 2,5-dimethyoxytetrahydrofuran (mixture of cis- and trans-isomers). The pyrrole 14 was then deprotonated at the hydroxyl position by use of sodium hydride in dry tetrahydrofuran (THF) at 0° C. for 1 h followed by coupling an equimolar quantity of the α-bromo-arylester 12 in dry THF overnight to produce the ethylester-acetamide 15. Hydrolysis of the ethyl ester 15 to the corresponding acid 16 was achieved using a 10% sodium hydroxide solution in ethanol/THF (1:1), stirring at room temperature for 2 h.

(4-Methoxy-phenyl)-(2-pyrrol-1-yl-pyridin-3-yloxy)-acetic acid (16a)

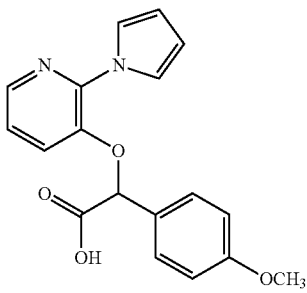 [SMILES: COc1ccc(C(Oc2cccnc2-n2cccc2)C(=O)O)cc1]

MS-ESI: m/z 325.1 (99%, M+1). $^1$H-NMR (CD$_3$OD) δ 3.84 (3H, s), 5.89 (1H, s), 6.31 (2H, t, J=2.4 Hz), 6.96 (2H, d, J=9 Hz), 7.22 (1H, q), 7.50 (2H, d, J=9 Hz), 7.57 (1H, d), 7.74 (2H, t, J=2.4 Hz), 8.06 (1H, dd).

(4-Methoxy-phenyl)-(2-pyrrol-1-yl-phenoxy)-acetic acid (16b)

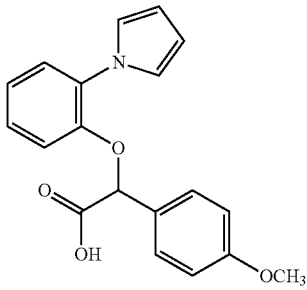 [SMILES: COc1ccc(C(Oc2ccccc2-n2cccc2)C(=O)O)cc1]

MS-ESI: m/z 323.9 (50%, M+1). $^1$H-NMR (CDCl$_3$) δ 3.79 (3H, s), 5.43 (1H, s), 6.34 (2H, t), 6.88 (2H, d, J=8.7 Hz), 6.97 (1H, d, J=2.3 Hz), 7.06 (2H, t), 7.07 (1H, s), 7.21 (1H, d, J=2.3 Hz), 7.35 (2H, d, J=8.7 Hz), 7.36 (1H, s). CHN Anal. C (Calc. 70.58. Found 67.34). H (Calc. 5.30. Found 5.39). N (Calc. 4.33. Found 4.12).

(4-Fluoro-phenyl)-(2-pyrrol-1-yl-phenoxy)-acetic acid (16c)

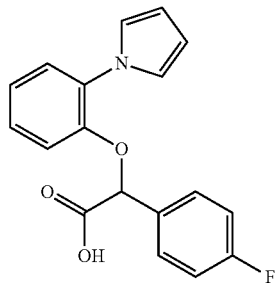 [SMILES: O=C(O)C(Oc1ccccc1-n1cccc1)c1ccc(F)cc1]

MS-ESI: m/z 310.3 (30%, M−1). $^1$H-NMR (CDCl$_3$) δ 5.46 (1H, s), 6.33 (2H, t), 6.96 (1H, dd), 7.03-7.05 (3H, m), 7.10 (1H, dd), 7.20 (1H, dd), 7.34 (1H dd), 7.38-7.44 (3H, m). CHN Anal. C (Calc. 69.45. Found 67.27). H (Calc. 4.53. Found 4.53). N (Calc. 4.50. Found 3.84).

(4-Chloro-2-pyrrol-1-yl-phenoxy)-(4-methoxy-phenyl)-acetic acid (16d)

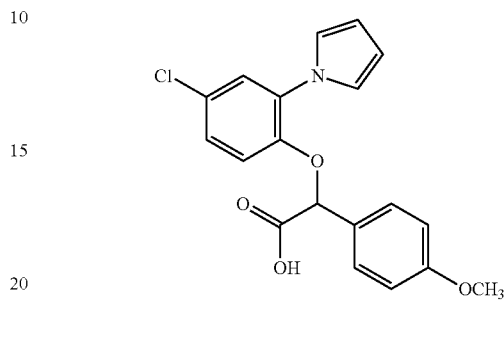

MS-ESI: m/z 379.9 (99%, M+1, as sodium salt). $^1$H-NMR (CDCl$_3$) δ 3.79 (3H, s), 5.38 (1H, s), 6.31 (2H, t), 6.85 (2H, d, J=9 Hz), 7.01 (1H, d), 7.05 (2H, t), 7.14 (1H, dd), 7.24 (2H, d, J=9 Hz), 7.31 (1H, d).

3. Synthesis of Acetamide Ligands

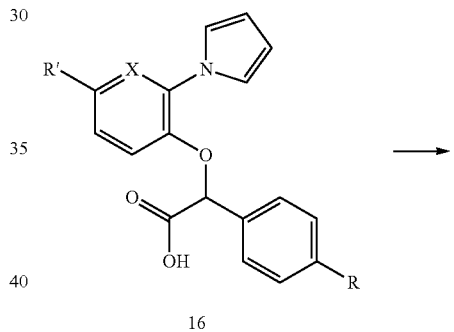

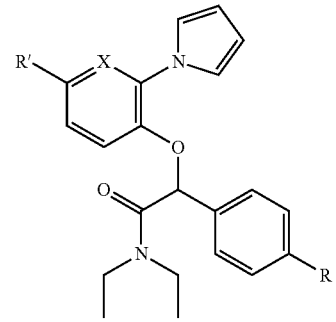

R=OH, CH$_3$, OCH$_3$, NO$_2$, F, Cl, naphthyl; R'=H, Cl; X=N, CH.

Scheme 8: Acetamide synthesis. Reagents: EEDQ, TEA, DEA.

General Procedure for Synthesis of Acetamide Compounds 19

The carboxylic acid 16 was dissolved in dry THF and to this was added an excess of the initiator 2-ethoxy-1-ethoxycarbonyl-1,2-dihydroquinoline (EEDQ), triethylamine and diethylamine. The reaction was refluxed for 8-12 h and was monitored for completion by TLC, producing the acetamide 19.

N,N-Diethyl-2-(4-methoxy-phenyl)-2-(2-pyrrol-1-yl-pyridin-3-yloxy)-acetamide (19a)

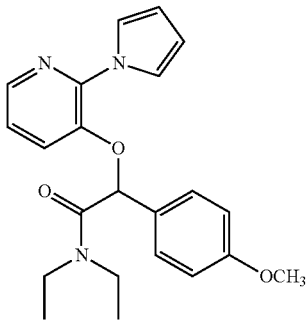 [SMILES: CCN(CC)C(=O)C(Oc1cccnc1-n1cccc1)c1ccc(OC)cc1]

MS-ESI: m/z 380.0 (35%, M+1). $^1$H-NMR (CDCl$_3$) δ 0.88 (3H, t), 1.09 (3H, t), 3.20 (2H, q), 3.35 (2H, q), 3.80 (3H, s), 5.65 (1H, s), 6.30 (2H, t), 6.89 (2H, d, J=8.7 Hz), 7.05 (1H, dd), 7.33 (1H, m), 7.32 (2H, d, J=8.7 Hz), 7.65 (2H, t), 8.11 (1H, dd).

N,N-Diethyl-2-(4-methoxy-phenyl)-2-(2-pyrrol-1-yl-phenoxy)-acetamide (19b)

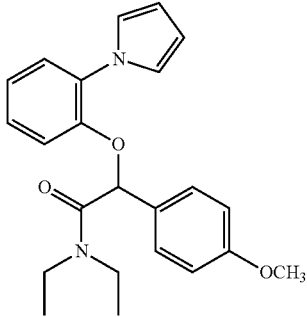 [SMILES: CCN(CC)C(=O)C(Oc1ccccc1-n1cccc1)c1ccc(OC)cc1]

MS-ESI: m/z 378.3 (25%, M). $^1$H-NMR (CDCl$_3$) δ 0.75 (3H, t), 1.05 (3H, t), 3.21 (2H, q), 3.31 (2H, q), 3.79 (3H, s), 5.61 (1H, s), 6.32 (2Hm t), 6.84 (2H, d, J=9 Hz), 7.05 (2H, t), 7.22 (1H, m), 7.27 (1H, s), 7.31 (2H, d), 7.34 (2H, m).

2-(4-Chloro-2-pyrrol-1-yl-phenoxy)-N,N-diethyl-2-(4-methoxy-phenyl)-acetamide (19d)

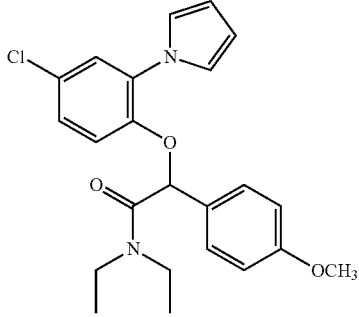 [SMILES: CCN(CC)C(=O)C(Oc1ccc(Cl)cc1-n1cccc1)c1ccc(OC)cc1]

MS-ESI: m/z 412.3 (92%, M). $^1$H-NMR (CDCl$_3$) δ 0.85 (3H, t), 1.05 (3H, t), 3.10 (2H, q), 3.76 (2H, q), 3.88 (3H, s), 5.50 (1H, s), 6.32 (2H, t), 6.86 (3H, dd), 7.06 (2H, t), 7.17 (1H, d), 7.22, (1H, s), 7.31 (1H, d), 7.44 (1H, d).

It will be appreciated that it is well within the competence of the skilled addressee to synthesise compounds of formula (IV) with minor modifications to the above-mentioned parameters. For example, by varying reaction times, temperatures, molar ratios and by varying the appropriate starting reagents. Further compounds synthesised via this route include

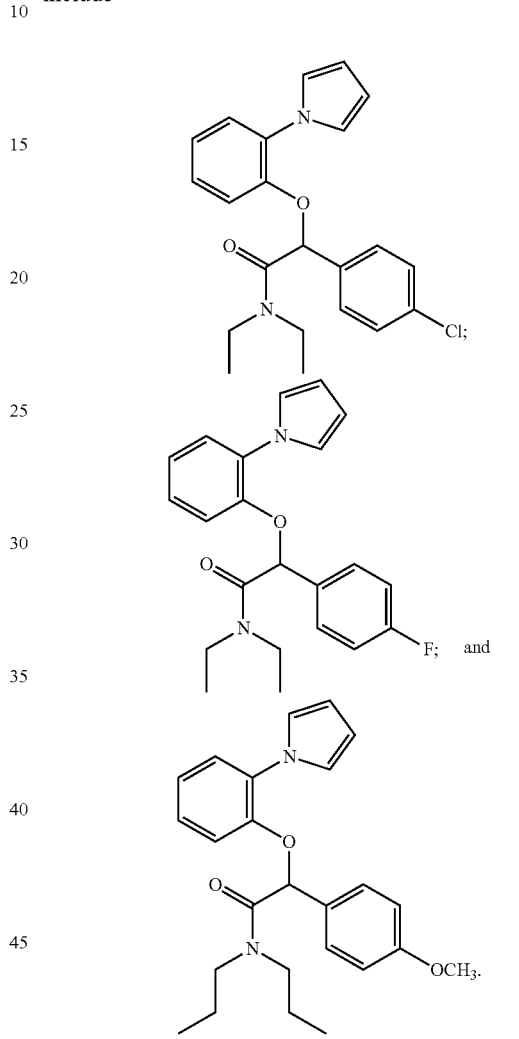

Another compound of particular interest is

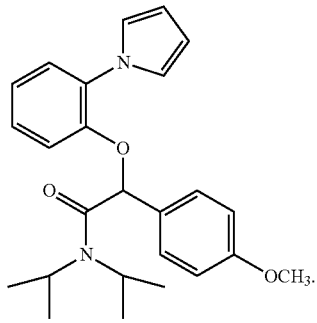 [SMILES: COc1ccc(C(Oc2ccccc2-n2cccc2)C(=O)N(C(C)C)C(C)C)cc1]

4. Resolution of Chiral Carboxylic Acids 16.

The carboxylic acid 16 can be resolved according to the general procedure outline in *J. Med. Chem.*, 1991, Vol. 34, No. 9, 2864. The resolved carboxylic acid 16 can be converted to the acetamide by the general procedure for synthesis of acetamide compounds 19, as illustrated in schemes 8 and 9.

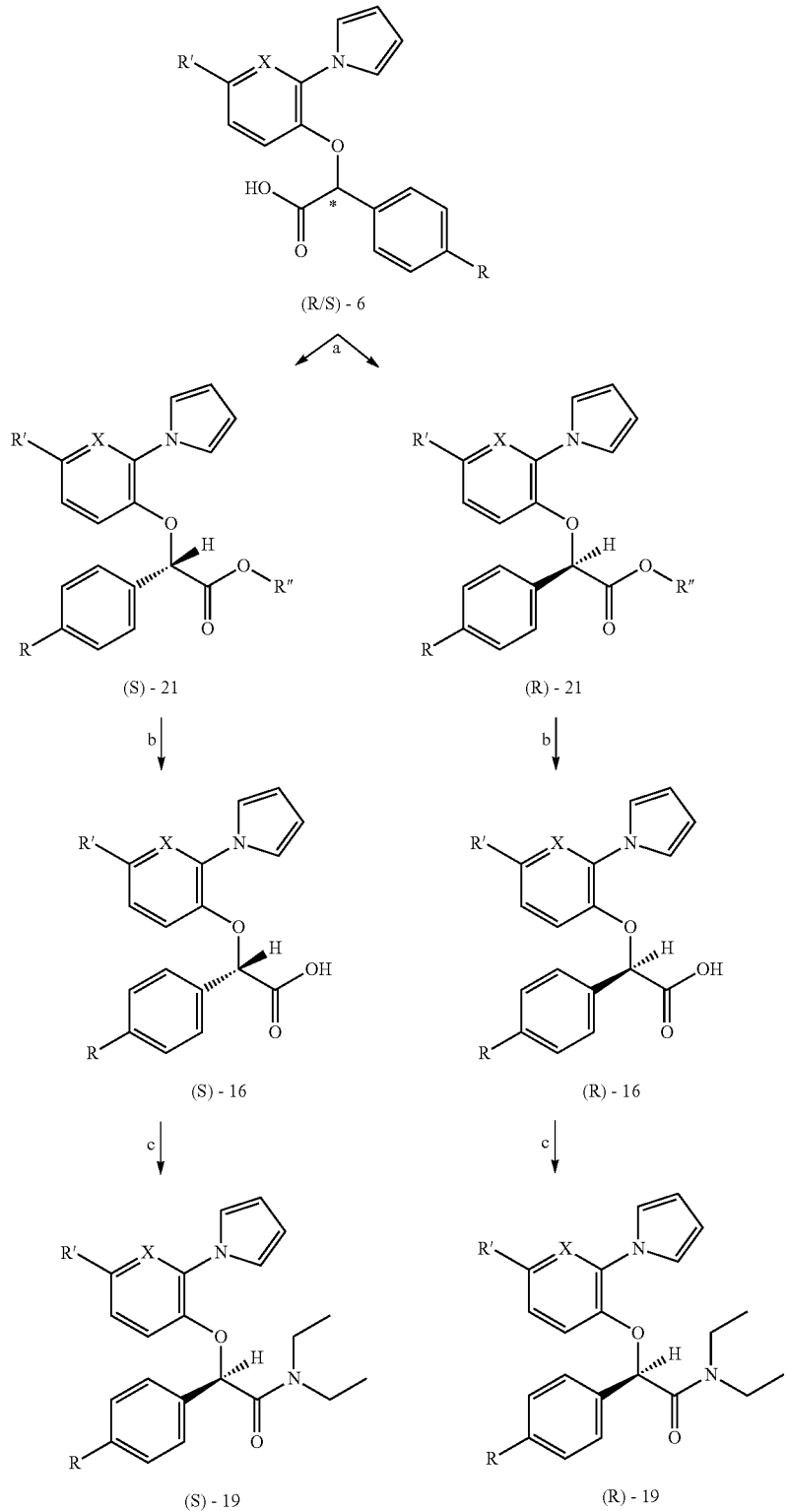

Scheme 9: Reagents (a) Oxalyl chloride, N-methylpyrrolidine, (R)-(-)-pantolactone or D-(+)-Ribonic acid-γ-lactone (b) 2 N HCl, AcOH (c) EEDQ, DEA, TEA.

-continued

R = OH, CH₃, OCH₃, NO₂, F, Cl, naphthyl; R' = H, Cl; X = N, CH;

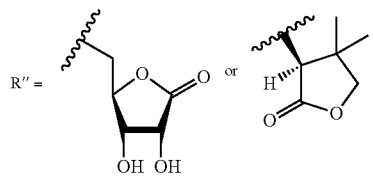

5. In Vitro Binding Affinity

3H-PK11195 (specific activity 322 GBq/mmol) and 3H-Ro 15-1788 (specific activity 311 GBq/mmol) were purchased from Dupont-New England Nuclear. For binding studies, mitochondria were prepared as described in Trapani G., et al. *J Med Chem.* 1997; 40:3109-3118, with minor modifications as described here, from the kidneys of male Wistar rats killed by cervical dislocation. The kidneys were homogenized in 20 volumes of ice-cold 50 mM Tris-HCl (pH 7.4), 0.32 M sucrose, and 1 mM ethylenediaminetetraacetic acid (buffer A) containing protease inhibitors (benzamidine at 160 mg/mL, bacitracin at 200 mg/mL, and soybean trypsin inhibitor at 20 mg/mL) with a Teflon (DuPont) pestle in a glass homogenizer and centrifuged at 600 g for 10 min at 4° C. The resulting supernatant was centrifuged at 10,000 g for 10 min at 4° C. The pellet was suspended in 20 volumes of ice cold buffer A and centrifuged at 10,000 g for 10 min at 4° C. The crude mitochondrial pellet was frozen at −20° C. until the time of the assay or incubated with 0.6 nM 3H-PK11195 in 50 mM Tris-HCl (pH 7.4) (buffer B) with a range of concentrations of the tested compounds (0.1 nM-10 mM) in a total volume of 0.5 mL for 90 min at 4° C. The incubation was terminated by dilution to 5 mL with icecold buffer B; this step was followed immediately by rapid filtration through glass fiber Whatman GF/C filters. The filters were washed (2.5 mL) with buffer B, and the amount of radioactivity retained on the filters was determined with a Packard 1600 TR liquid scintillation counter at 66% efficiency. Nonspecific binding was estimated for each sample in the presence of unlabeled 1 mM PK11195. The 50% inhibitory concentrations were determined, and the dissociation constant (Ki) values were derived according to a previously derived equation (Cheng Y., et al. *Biochem Pharmacol.* 1973; 22:3099-3108). The protein concentration was estimated by the method of Lowry et al. (*J Biol Chem.* 1951; 193:265-275) with bovine serum albumin (Sigma-Aldrich) as the standard.

| Compound | $K_i$ (nM) TSPO |
|---|---|
| [structure with OCH₃] | 2.61 |
| [structure with CH₃] | 0.46 |
| [structure with Cl] | 0.45 |
| [structure with Br] | 0.97 |
| [structure with F] | 2.40 |

49
-continued

| Compound | $K_i$ (nM) TSPO |
|---|---|
| 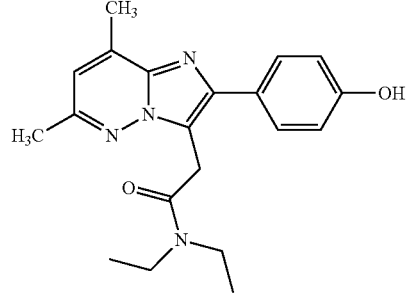 [SMILES: CCN(CC)C(=O)Cc1c(-c2ccc(O)cc2)nc2c(C)cc(C)nn12] | 10.96 |
| 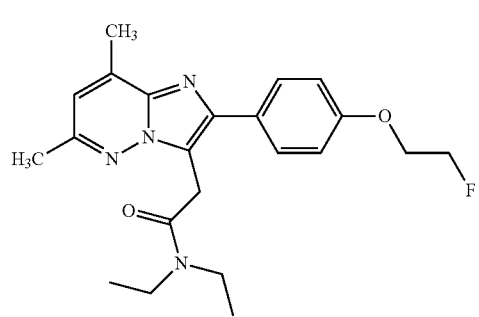 [SMILES: CCN(CC)C(=O)Cc1c(-c2ccc(OCCF)cc2)nc2c(C)cc(C)nn12] | 1.55 |
| 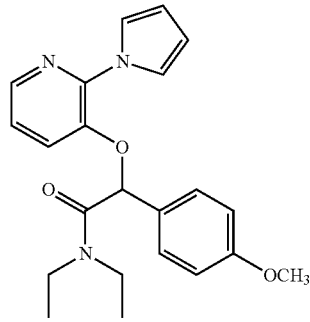 | 4.0 |
| 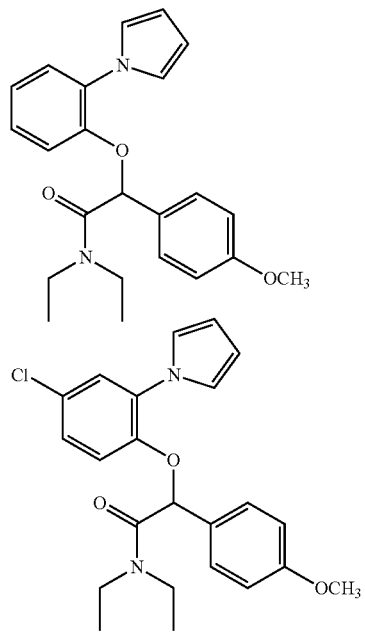 | 5.0 |
| (structure with Cl, pyrrole, OCH3) | 5.7 |

50

6. Radiolabelling with [$^{18}$F]

Scheme 10: Radiolabelling with $^{18}$F.

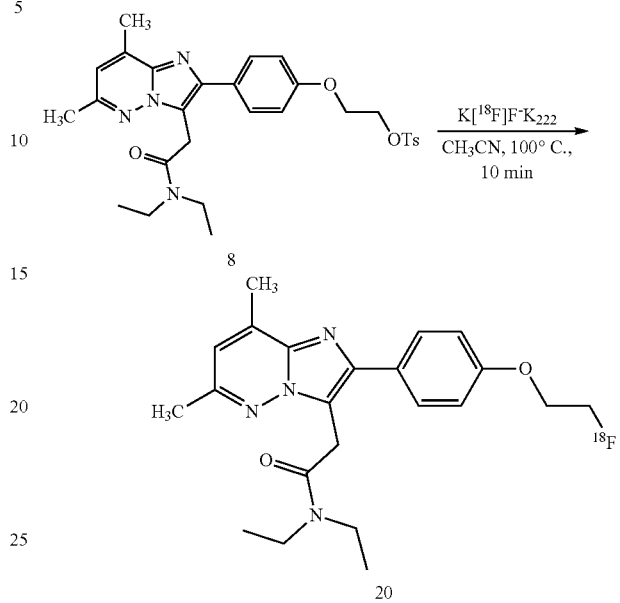

The skilled artesian will appreciate that compounds of formula (III) or (IV) may be radiolabelled at any position on the compound. For example, compounds of formula (III) or (IV) may be radiolabelled on the phenyl substituent via an ethoxy group using a tosyl or fluoro precursor, or the acetamide functional group may be labelled directly by employing a tosyl or fluoro precursor.

Radiosynthesis of [$^{18}$F]PDAZ-FE (20)

Radioisotope production. No carrier added-aqueous [$^{18}$F] fluoride ion was produced on a PETtrace cyclotron (GE Healthcare, Sweden) by irradiation of a 0.8 mL silver bodied water target using a 25 μA current and a 16.5 MeV proton beam on 95% enriched [$^{18}$O]H$_2$O by the [$^{18}$O(p, n)$^{18}$F] nuclear reaction.

Preparation of K[$^{18}$F]F-Kryptofix 2.2.2. [$^{18}$F]Fluoride in [$^{18}$O]H$_2$O was transferred to the GE TRACERlab FX$_{F-N}$ synthesiser and passed through an anion exchange resin (Sep-Pak Waters Accell™ Light QMA cartridge in the carbonate form, prepared by washing with 10 mL 0.5 M K$_2$CO$_3$ and then rinsed with 10 mL of water and dried with N$_2$ under vacuum. Trapped [$^{18}$F]fluoride was then eluted from the Sep-Pak cartridge and transferred to the reactor vessel using an eluent [containing K$_2$CO$_3$ (4 mg), Kryptofix 222 (13 mg), sterile water 100 μL and acetonitrile (900 μL)] and was then evaporated by heating at 70° C. under helium flow and vacuum. Acetonitrile (1 mL) was subsequently added to the reaction vessel and evaporated to dryness by heating at 120° C. under vacuum.

Preparation and formulation of [$^{18}$F]PDAZ-FE. The tosyl precursor (8, 2 mg) was dissolved in acetonitrile (1 mL) and added to the dry K[$^{18}$F]F-Kryptofix 2.2.2 complex. The mixture was allowed to react at 100° C. for 10 min. Upon completion, the reaction mixture was diluted with sterile water (1 mL) and transferred to a separate receptacle. The reactor vessel was rinsed with sterile water (0.5 mL) and transferred to the same receptacle. The entire crude mixture (contained within the receptacle) was then injected onto a HPLC Waters XTerra RP C-18 (10 μm, 7.8×300 mm) semi-preparative reversed phase column (contained within the same hot cell as the TRACERlab $FX_{F-N}$ module). Using a mobile phase of 0.1 M $NH_4Ac$ (pH 10):$CH_3CN$; (65:35, v:v), and with a flow rate of 4.0 mL/min, the $t_R$ of [$^{18}F$]PDAZ-FE was 25 min. The radioactive fraction corresponding to [$^{18}F$] PDAZ-FE was collected into a round bottom flask containing sterile water (40 mL). This entire solution was subsequently passed through a tC-18 Sep-Pak cartridge. The tC18 trapped radio-labelled product was further rinsed with sterile water (5 mL). The product was then eluted from the tC18 Sep-Pak cartridge with EtOH (0.5 mL) and sterile water (5 mL) and then filtered through a sterile 13 mm Millipore GS 0.22 μm filter into a 10 mL sterile pyrogen free vial.

Quality control of [$^{18}F$] PDAZ-FE. For determination of specific radioactivity and radiochemical purity, an aliquot of the final solution of known volume and radioactivity was injected onto an analytical reversed phase HPLC column Phenomenex Luna RP C-18 column, (5 μm, 4.6×250 mm) and a mobile phase of $H_2O$:TFA:ACN (65:0.01:35, v:v) at a flow rate of 1 mL/min. With these conditions [$^{18}F$]PDAZ-FE had a retention time ($t_R$) of 6.2 min. The area of the UV absorbance peak measured at 254 nm corresponding to the carrier product was measured (integrated) on the HPLC chromatogram and compared to a standard curve relating mass to UV absorbance. Tosylate precursor (compound 8) displayed a $t_R$ of 31.6 min.

[$^{18}F$]PDAZ-FE Normal Rat MicroPET Studies

All PET data was acquired using a MicroPET Focus 220 animal scanner. The rat was initially anaesthetised using isoflurane (Troy Laboratories Pty Ltd, Australia) gas (5% for induction and 1-4% for maintenance). The head of the rat was immobilised with a perspex stereotactic frame to minimise motion artifacts. A $^{57}Co$ rod source was used for a (8 min) transmission scan of the head just prior to the emission study for the purpose of attenuation correction. Acquisition of the PET data in list mode was commenced just prior to administration of 60 MBq of [$^{18}F$]PDAZ-FE in 100 μL of sterile water, and was continued for a period of 60 min. At the conclusion of each study the list mode data were sorted into a dynamic sinogram comprising 24 frames (10×30 s, 5×120 s and 9×300 s). The dynamic 3-D PET sinograms were reconstructed with 3D reprojection (zoom 4.745) into 95 transaxial slices, each comprising 128×128 voxels. Reconstructed voxel values in each frame were in units of Bq/mL, corrected for radioactive decay to the time of injection and voxel dimensions were 0.400×0.400×0.796 cm. Voxel values were then converted to units of standard uptake value (SUV) and then into % injected dose/mL. TACs representing the variation in ligand concentration vs time was constructed for the whole brain. After the list-mode acquisition, a whole body PET scan was performed, 5 min at four different bed positions, to determine total activity in the whole body. Attenuation, scatter and dead time corrections were applied to all data.

A second study involved pre-treating the rat with PK11195 (3 mg/kg) 5 min prior to [$^{18}F$]PDAZ-FE (26 MBq in 100 μL sterile water). Both PK11195 and the radioligand were administered via the rat tail vein. FIG. 1 shows a MicroPET image taken of rat administered with [$^{18}F$]PDAZ-FE, and of a rat administered with [$^{18}F$]PDAZ-FE which has been pre-treated with PK11195.

Although the invention has been described with reference to specific examples, it will be appreciated by those skilled in the art that the invention may be embodied in many other forms.

The invention claimed is:

1. A compound of formula (III)

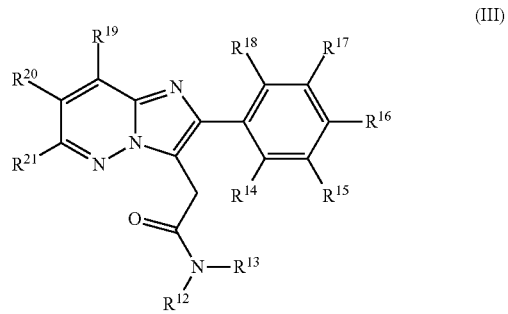

(III)

wherein $R^{12}$ and $R^{13}$ are each independently selected from the group consisting of H, benzyl, $C_1$-$C_{10}$ alkyl, $C_2$-$C_{10}$ alkenyl, $C_2$-$C_{10}$ alkynyl, aryl and heteroaryl, each of which may optionally be substituted with one or more of halo or $C_1$-$C_6$ alkyl;

or $R^{12}$ and $R^{13}$, together with the nitrogen to which they are attached, form an optionally substituted heterocyclic ring having between 3 and 7 ring members;

$R^{14}$, $R^{15}$, $R^{16}$, $R^{17}$ and $R^{18}$ are each independently H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{22}$, $(CH_2)_nOR^{22}$ or an optionally substituted polyether;

$R^{19}$ and $R^{21}$ are each independently halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{22}$, $(CH_2)_nOR^{22}$ or an optionally substituted polyether;

$R^{20}$ is H, halo, OH, $NO_2$, optionally substituted alkyl, optionally substituted alkoxy, optionally substituted alkenyl, optionally substituted alkynyl, optionally substituted aryl, optionally substituted heteroaryl, optionally substituted $NHC_{1-6}$ alkyl, optionally substituted $SC_{1-6}$ alkyl, $COOR^{22}$, $(CH_2)_nOR^{22}$ or an optionally substituted polyether;

$R^{22}$ is optionally substituted alkyl; and n is an integer from 1 to 6;

or a salt or solvate thereof.

2. The compound according to claim 1 wherein $R^{20}$ is H; $R^{19}$ and $R^{21}$ are each independently $C_{1-6}$ alkyl; $R^{14}$, $R^{15}$, $R^{16}$, $R^{17}$ and $R^{18}$ are each independently H, halo, OH, $NO_2$, optionally substituted $C_{1-6}$ alkyl, optionally substituted $OC_{1-6}$ alkyl or optionally substituted aryl; $R^{16}$ is halo, OH, optionally substituted $C_{1-6}$ alkyl or optionally substituted $OC_{1-6}$ alkyl; and $R^{12}$ and $R^{13}$ are each independently a $C_{1-6}$ alkyl.

3. The compound according to claim 1 selected from the group consisting of:

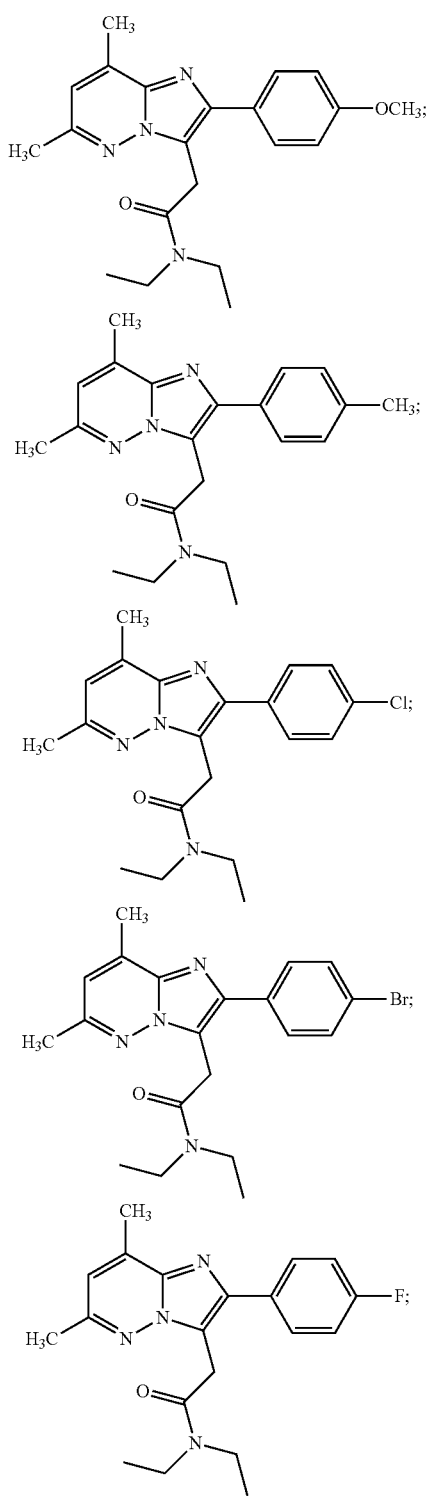

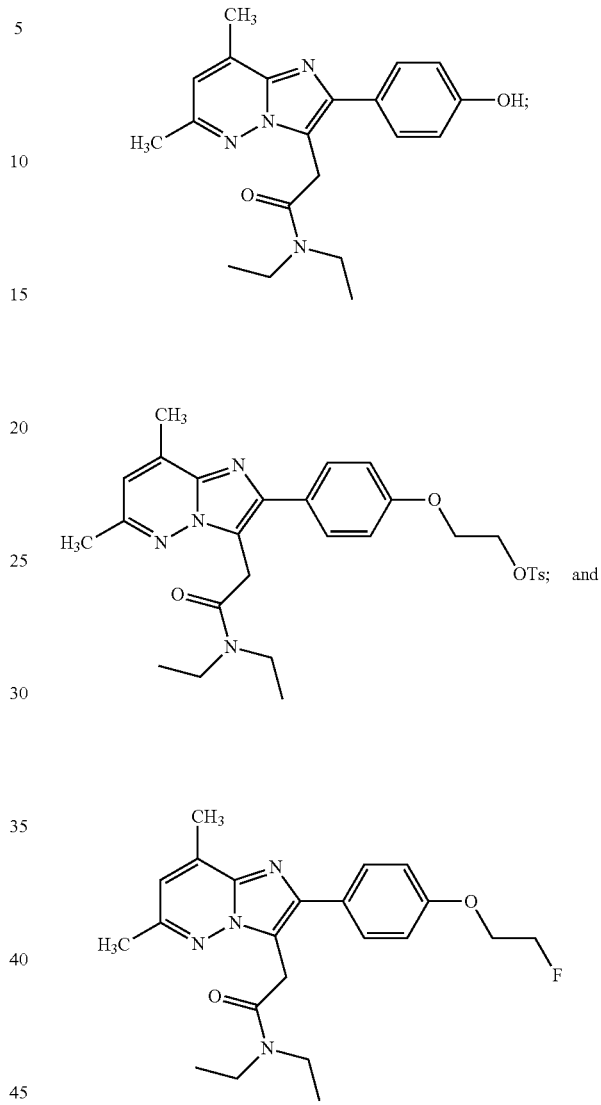

or a salt or solvate thereof.

4. The compound according to claim 1 radiolabelled with a radioisotope.

5. The compound according to claim 4 wherein said radioisotope is selected from $^{18}F$, $^{123}I$, $^{76}Br$, $^{124}I$ and $^{75}Br$.

6. A pharmaceutical composition comprising a compound according to claim or a pharmaceutically acceptable salt thereof, and a pharmaceutically acceptable carrier.

* * * * *